US008273750B2

(12) United States Patent
Li et al.

(10) Patent No.: US 8,273,750 B2
(45) Date of Patent: Sep. 25, 2012

(54) ORGANIC COMPOUNDS

(75) Inventors: Peng Li, New York, NY (US); Haiyan Wu, New York, NY (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 11/916,761

(22) PCT Filed: Jun. 6, 2006

(86) PCT No.: PCT/US2006/022066
§ 371 (c)(1),
(2), (4) Date: Dec. 6, 2007

(87) PCT Pub. No.: WO2006/133261
PCT Pub. Date: Dec. 14, 2006

(65) Prior Publication Data
US 2008/0188492 A1 Aug. 7, 2008

Related U.S. Application Data

(60) Provisional application No. 60/687,715, filed on Jun. 6, 2005.

(51) Int. Cl.
*C07D 487/00* (2006.01)
(52) U.S. Cl. .................................. 514/257; 544/247
(58) Field of Classification Search .................. 514/257; 544/247, 251
See application file for complete search history.

(56) References Cited

U.S. PATENT DOCUMENTS

| 5,294,612 | A | 3/1994 | Bacon et al. |
| 5,393,755 | A | 2/1995 | Neustadt et al. |
| 5,824,683 | A | 10/1998 | McKittrick et al. |
| 5,849,770 | A | 12/1998 | Head et al. |
| 5,939,419 | A | 8/1999 | Tulshian |
| 5,962,492 | A | 10/1999 | Warrellow et al. |
| 6,013,621 | A | 1/2000 | Nishi et al. |
| 6,133,273 | A | 10/2000 | Gilbert et al. |
| 6,235,742 | B1 | 5/2001 | Bell et al. |
| 6,235,746 | B1 | 5/2001 | Davis et al. |
| 6,316,444 | B1 | 11/2001 | Hunt et al. |
| 6,423,716 | B1 | 7/2002 | Matsuno et al. |
| 6,492,371 | B2 | 12/2002 | Roylance |
| 6,498,165 | B1 | 12/2002 | Armstrong et al. |
| 6,552,029 | B1 | 4/2003 | Davis et al. |
| 6,582,423 | B1 | 6/2003 | Thapliyal et al. |
| 6,599,908 | B1 | 7/2003 | Davis et al. |
| 6,649,608 | B2 | 11/2003 | Pease et al. |
| 6,670,368 | B1 | 12/2003 | Breault et al. |
| 6,693,099 | B2 | 2/2004 | Degenhardt et al. |
| 6,969,719 | B2 | 11/2005 | Asberom et al. |
| 7,153,824 | B2 | 12/2006 | Palmer et al. |
| 2003/0069246 | A1 | 4/2003 | Darrow et al. |
| 2003/0162782 | A1 | 8/2003 | Grossman et al. |
| 2004/0087517 | A1 | 5/2004 | Burnet et al. |
| 2008/0176961 | A1 | 7/2008 | Greengard et al. |
| 2008/0193964 | A1 | 8/2008 | Greengard et al. |
| 2008/0194592 | A1 | 8/2008 | Mates et al. |
| 2010/0087450 | A1 | 4/2010 | Mates et al. |
| 2010/0173878 | A1 | 7/2010 | Li et al. |
| 2010/0273754 | A1* | 10/2010 | Li ............................. 514/171 |

FOREIGN PATENT DOCUMENTS

| DE | 19931206 | 1/2001 |
| EP | 0 063 381 | 4/1982 |
| EP | 0201188 | 12/1986 |
| EP | 0911333 | 4/2002 |
| JP | 53031694 | 3/1978 |
| WO | WO91/19717 | 12/1991 |
| WO | WO94/19351 | 9/1994 |
| WO | WO 98/46606 | 10/1998 |
| WO | WO98/52568 | 11/1998 |
| WO | WO03/002567 | 1/2003 |
| WO | WO03/020702 | 3/2003 |
| WO | WO 03/020724 | 3/2003 |
| WO | WO03/042216 | 5/2003 |
| WO | WO2007/143705 | 12/2007 |
| WO | WO 2009/073210 | 6/2009 |
| WO | WO 20091075784 | 6/2009 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Vatter, et al., Differential Phosphodiesterase Expression and Cytosolic Ca in Human CNS Tumour Cells and in Non-Malignant and Malignant Cells of Rat Origin, J. of Neurochemistry, 93, 321-329 (2005).*
Vatter, et al., Differential Phosphodiesterase Expression and Cytosolic Ca2+ in Human CNS Tumour Cells and in Non-Malignant and Malignant Cells of Rat Origin, J. of Neurochemistry, 93, 321-329 (2005).*
Jiang, et al., Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol, J. Org. Chem., 70, 2824-2827 (2004).*
Xia, et al., Synthesis and Evaluation of Polycyclic Pyrazolo[3,4-d]pyrimidines as PDE1 and PDE5 cGMP Phosphodiesterase Inhibitors, J. Med. Chem., 40, 4372-77 (1997).*
Jiang, et al., Chemoenzymatic Asymmetric Total Synthesis of Phosphodiesterase Inhibitors: Preparation of a Polycyclic Pyrazolo[3,4-d]pyrimidine from an Acylnitroso Diels—Alder Cycloadduct-Derived Aminocyclopentenol, J. Org. Chem., 70, 2824-2827 (2004).*
Bastia et al., Effect of $A_1$ and $2_{2A}$ Adenosine Receptor Ligands in Mouse Acute Models of Pain, Neuroscience Letters (2002) 328:241-244.

(Continued)

*Primary Examiner* — Erich A Leeser
(74) *Attorney, Agent, or Firm* — Hoxie & Associates LLC

(57) ABSTRACT

The invention provides novel 7,8-dihydro-imidazo[1,2-α]pyrazolo[4,3-e]pyrimidin-4-one compounds and 7,8,9-trihydro-[1H or 2/f]-pyrimido[1,2-a]pyrazolo[4,3-e]pyrimidin-4(5H)-one compounds, substituted at the 1 or 2 position with C2-g allcyl, C3-9 cycloalkyl, heteroarylalkyl, or substituted arylalkyl, in free, salt or prodrug form, processes for their production, their use as pharmaceuticals, particularly as PDE1 inhibitors, and pharmaceutical compositions comprising them.

21 Claims, No Drawings

OTHER PUBLICATIONS

Chebib et al., 1-Phenylpyrazolo[3,4-d]pyrimidines; Structure-Activity Relationships for C6 Substituents at $A_1$ and $A_{2A}$ Adenosine Receptors, Bioorganic & Medicinal Chemistry (2000) 8:2581-2590.
Chermat et al., Journal Pharmacology (1986) 17: 348-350.
Lundqvist et al., Exploitation of Structural and Regulatory Diversity in Glutamate Racemases, Nature (2007) 447:817-822.
Mani et al., Science (2000) 287:1053.
Murray et al., LY503430, a Novel __-Amino-3-hydroxy-5-methylisoxazole-4-propionic Acid Receptor Potentiator with Functional, Neuroprotective and Neurotrophic Effects in Rodent Models of Parkinson's Disease, JPEJ, (2003) 306:752-762.
Porsolt et al., Nature (1977) 266:730-732.
Poulsen et al.High-Pressure Synthesis of Enantiomerically Pure C-6 Substituted Pyrazolo[3,4-d]pyrimidines, Biorganic & Medicinal Chemistry Letter (2001) 11:191-193.
Turko et al., Inhibition of Cyclic GMP-Binding Cyclic GMP-Specific Phosphodiesterase (Type 5) by Sildenafil and Related Compounds, Molecular Pharmacology (1990) 56:124-130.
Ungerstedt, Acta Physiology Second Suppl. (1971) 367:1-48.
Ungerstedt et al., Brain Research (1970) 24: 485-493.
Xia et al., Synthesis and Evaluation of Polycyclic Pyrazolo[3,4-d]pyrimidines as PDE1 and PDE5 cGMP Phosphodiesterase Inhibitors, Journal Medicinal Chemistry (1997) 40: 4372-4377.
Bender et al., "Cyclic Nucleotide Phosphodiesterases: Molecular Regulation to Clinical Use", Pharmcol. Rev., 2006, 58, pp. 488-520.
Fienberg et al., "DARPP-32: Regulator of the Efficacy of Dopaminergic Neurotransmission", Science, (1998) 281, pp. 838-842.
Greengard et al., "Beyond the Dopamine Receptor: the DARPP-32/Protein Phosphatase-1 Cascade", Neuron, 1999, 23, pp. 435,447.
Han et al., "The Calcium/Calmodulin-dependent Phosphodiesterase PDE1C Down-regulates Glucose-induced Insulin Secretion", J. Bio, Chem., 1999, 274(32), pp. 22337-22344.
Murray et al., "Expression and activity of cAMP phosphodiesterase isoforms in pulmonary artery smooth muscle cells from patients with pulmonary hypertension: role for PDE1", Am. J. Physiol. Lung Cell Mol. Physiol., 2007, 292, pp. L294-L303.
Reed et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning", The Journal of Neuroscience, 2002, 22(12), pp. 5188-5197.
Rybalkin et al., "Cyclic GMP Phosphodiesterases and Regulation of Smooth Muscle Function", Circ. Res., 2003, 93, pp. 280-291.
Shimizu et al., "Calmodulin-Dependent Cyclic Nucleotide Phosphodiesterase (PDE1) is a Pharmacological Target of Differentiation-Inducing Factor-1, an Antitumor Agent Isolated from Dictyostelium", Cancer Research, 2004, 64, pp. 2568-2571.
Ahn, H., et al., Potent Tetracyclic Guanine Inhibitors of PDE1 and PDE5 Cyclic Guanosine Monophosphate Phosphodiesterases with Oral Antihypertensive Activity, Journal of Medicinal Chemistry, 1997, pp. 2196-2210, vol. 40, No. 14, American Chemical Society, U.S.
Ahn, H., et al. Potent Tetracyclic Guanine Inhibitors of PDE1 and PDE5 Cyclic Guanosine Monophosphate Phosphodiesterases with Oral Antihypertensive Activity, J. Med. Chem. (1997) 40(14):2196-2210.
Burnouf et al., "Synthesis, Structure-Activity Relationships, and Pharmacological Profile of 9-Amino-4-Oxo-1-Phenyl-3,4,5,6,7-Tetrahydrol[1,4]Diazepino[6,7,1-hi]Indoles: Discovery of Potent, Selective Phosphodiesterase Type 4 Inhibitors," (2000), J. Med. Chem., 43:4850-4867.
U.S. Appl. No. 12/517,945, filed Dec. 5, 2007, Fienberg et al.
Polli et al., "Expression of a Calmodulin-Dependent Phosphodiesterase Isoform (PDE1B1) Correlates With Brain Regions Having Extensive Dopaminergic Innervation," (1994), The Journal of Neuroscience, 14:1251-1261.
Dewald et al., Synthesis and Potential Antipsychotic Activity of 1H-Imidazo[1,2-c]pyrazolo[3,4-e]pyrimidines, J. Med. Chem. 1988, 31, pp. 454-461.
Jiang et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol", J. Org. Chem, 2005, 70, pp. 2824-2827.

* cited by examiner

ORGANIC COMPOUNDS

STATEMENT REGARDING GOVERNMENT FUNDING

This invention was made, in part, with government support under Grant. No. 2R44MH067488 awarded by NIMH and Grant No. DAMD-17-03-1-0396 awarded by USAMRMC. The government has certain rights in the invention.

CROSS REFERENCE TO RELATED APPLICATIONS

This application is a 35 U.S.C. §371 National Phase Application of International Application No. PCT/US2006/022066, filed Jun. 6, 2006, claiming priority to U.S. Provisional Application No. 60/687,715, filed Jun. 6, 2005, the contents of each of which are incorporated herein by reference.

TECHNICAL FIELD

The present invention relates to novel 7,8-dihydro-imidazo[1,2-a]pyrazolo[4,3-e]pyrimidin-4-one compounds and 7,8,9-trihydro-[1H or 2H]-pyrimido[1,2-a]pyrazolo[4,3-e]pyrimidin-4(5H)-one compounds, processes for their production, their use as pharmaceuticals and pharmaceutical compositions comprising them. Of particular interest are novel compounds useful as inhibitors of phosphodiesterase 1 (PDE1), e.g., in the treatment of diseases involving disorders of the dopamine D1 receptor intracellular pathway, such as Parkinson's disease, depression and damage to cognitive function, e.g., in schizophrenia.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopamninergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of calcium dependent nucleotide cyclases, resulting in increased cAMP and cGMP. These cyclic nucleotides in turn activate protein kinase A (PKA; cAMP-dependent protein kinase) and/or protein kinase G (PKG; cAMP-dependent protein kinase) that phosphorylate downstream signal transduction pathway elements such as DARPP-32 (dopamine and cAMP-regulated phosphoprotein) and cAMP responsive element binding protein (CREB).

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium is linked to cell death in numerous disorders, particularly in neurodegenerative diseases such as Alzheimer's Parkinson's and Huntington's Diseases, and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, and cognitive impairment.

There is thus a need for compounds that selectively inhibit PDE1 activity, especially PDE1B activity.

SUMMARY OF THE INVENTION

The invention provides novel, optionally substituted 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, substituted at the 1 or 2 position with $C_{2-9}$ alkyl or $C_{3-9}$ cycloalkyl, or optionally substituted heteroarylalkyl or substituted arylalkyl, in free, salt or prodrug form (hereinafter "Compounds of the Invention"). The 1- or 2-position substituent is preferably substituted benzyl or pyridylmethyl, e.g. para-substituted relative to the point of attachment, e.g., with aryl, e.g., phenyl, or heteroaryl, e.g., pyridyl or thiadiazolyl. These compounds are surprisingly found to selectively inhibit phosphodiesterase 1 (PDE1) activity, especially PDE1B activity.

Preferably, the Compounds of the Invention are the 7,8-dihydro-[1H or 2H]-imidazo[1,2-a]pyrazolo[4,3-e]pyrimidin-4(5H)-ones and 7,8,9-trihydro-[1H or 2H]-pyrimido[1,2-a]pyrazolo[4,3-e]pyrimidin-4(5H)-ones, of formula I

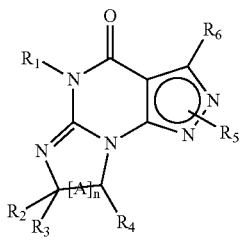

Formula 1 wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl
or
$R_5$ is attached to one of the nitrogens on the pyrazolo portion of Formula I and is a moiety of Formula A

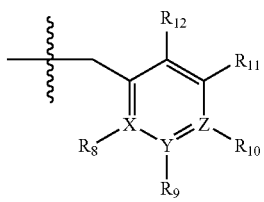

Formula A wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and
(iv) $R_6$ is H, alkyl, aryl, heteroaryl, arylalkyl (e.g., benzyl), arylamino (e.g., phenylamino), hetarylamino, N,N-dialkylamino, N,N-diarylamino, or N-aryl-N-(arylakyl)amino (e.g., N-phenyl-N-(1,1'-biphen-4-ylmethyl)amino); and
(v) n=0 or 1;
(vi) when n=1, A is —C($R_{13}R_{14}$)—
wherein $R_{13}$ and $R_{14}$, are, independently, H or $C_{1-4}$ alkyl, aryl, heteroaryl, (optionally hetero)arylalkoxy or (optionally hetero)arylalkyl;
in free, salt or prodrug form, including its enantiomers, diastereoisomers and racemates.

The invention further provides compounds of Formula I as follows:
1.1 Formula I wherein $R_1$ is methyl and n=0;
1.2 Formula I or 1.1 wherein $R_4$ is H or $C_{1-4}$ alkyl and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;
1.3 Formula I or 1.1 wherein $R_4$ is H and at least one of $R_2$ and $R_3$ is arylalkoxy;
1.4 Formula I wherein $R_1$ is methyl, $R_2$, $R_3$, and $R_4$ are H, n=1, and $R_{13}$ and $R_{14}$ are, independently, H or $C_{1-4}$ alkyl (e.g., methyl or isopropyl);
1.5 Formula I or 1.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;
1.6 Formula I, 1.1 or 1.5 wherein $R_5$ is a substituted heteroarylmethyl, e.g., para-substituted with haloalkyl;
1.7 Formula I, 1.1, 1.2, 1.3, 1.4 or 1.5 wherein $R_5$ is a moiety of Formula A wherein $R_8$, $R_9$, $R_{11}$, and $R_{12}$ are H and $R_{10}$ is phenyl;
1.8 Formula I, 1.1, 1.2, 1.3, 1.4 or 1.5 wherein $R_5$ is a moiety of Formula A wherein $R_8$, $R_9$, $R_{11}$, and $R_{12}$ are H and $R_{10}$ is pyridyl or thiadiazolyl,
1.9 Formula I, 1.1, 1.2, 1.3, 1.4 or 1.5 wherein $R_5$ is a moiety of Formula A wherein $R_8$, $R_9$, $R_{11}$, and $R_{12}$ are, independently, H or halogen, and $R_{10}$ is haloalkyl;
1.10 Formula I, 1.1, 1.2, 1.3, 1.4 or 1.5 wherein $R_5$ is a moiety of Formula A wherein $R_8$, $R_9$, $R_{11}$, and $R_{12}$ are, independently, H, and $R_{10}$ is alkyl sulfonyl;
1.11 any of the preceding formulae wherein $R_5$ is attached to the 2-position nitrogen on the pyrazolo ring;
1.12 any of the preceding formulae wherein $R_6$ is benzyl;
1.13 any of the preceding formulae wherein $R_6$ is phenylamino or phenylalkylamino (e.g., benzylamino);
1.14 any of the preceding formulae wherein $R_6$ is phenylamino;
1.15 any of the preceding formulae wherein X, Y, and Z are all C;
1.16 any of the preceding formulae wherein X, Y, and Z are all C and $R_{10}$ is phenyl or 2-pyridyl; and/or
1.17 any of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 24;
in free or salt form.

For example, the Compounds of the Invention include 7,8-dihydro-[1H or 2H]-imidazo[1,2-a]pyrazolo[4,3-e]pyrimidin-4(5H)-ones of Formula Ia

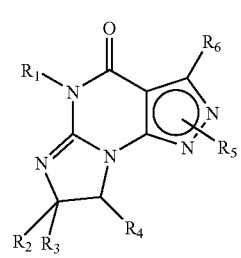

Formula Ia wherein
(i) $R_1$ is H or $C_{1-4}$ allyl [e.g., methyl];
(ii) $R_4$ is H and $R_2$ and $R_3$ are, independently, H or $C_{1-4}$ alkyl [e.g., $R_2$ and $R_3$ are both methyl, or $R_2$ is H and $R_3$ is isopropyl], aryl, or arylalkyl;

or $R_2$ is H and $R_3$ and $R_4$ together form a di-, tri- or tetramethylene bridge [pref. wherein the $R_3$ and $R_4$ have the cis configuration, e.g., where the carbons carrying $R_3$ and $R_4$ have the R and S configurations respectively];

(iii) $R_5$ is attached to one of the nitrogens on the pyrazolo portion of formula I and is a substituted benzyl of formula B

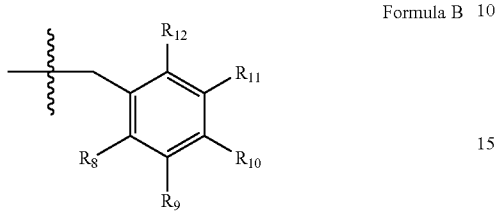

Formula B wherein $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl) aryl (e.g., phenyl), heteroaryl (e.g., pyridyl (for example pyrid-2-yl), or thiadiazolyl (e.g., 1,2,3-thiadiazol-4-yl)), arylcarbonyl (e.g., benzoyl), alkyl sulfonyl or heteroarylcarbonyl; and (iv) $R_6$ is H, alkyl, aryl, heteroaryl, arylalkyl [e.g., benzyl], arylamino [e.g., phenylamino], heteroarylamino, arylalkylamino, N,N-dialkylamino, N,N-diarylamino, or N-aryl-N-(arylalkyl)amino [e.g. N-phenyl-N-(1,1'-biphen-4-ylmethyl)amino];

in free, salt or prodrug form.

The invention further provides compounds of Formula Ia as follows:

1.1: Formula Ia wherein $R_1$ is methyl;
1.2: Formula Ia or 1.1 wherein $R_4$ is H and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;
1.3: Formula Ia or 1.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;
1.4: Formula Ia, 1.1, 1.2 or 1.3 wherein $R_5$ is a moiety of formula B wherein $R_8$, $R_9$, $R_{11}$, and $R_{12}$ are H and $R_{10}$ is phenyl;
1.5: Formula Ia, 1.1, 1.2, or 1.3 wherein $R_5$ is a moiety of formula B wherein $R_8$, $R_9$, $R_{11}$, and $R_{12}$ are H and $R_{10}$ is pyridyl or thiadiazolyl;
1.6: Formula Ia, 1.1, 1.2, 1.3, 1.4, or 1.5 wherein $R_5$ is attached to the 2-position nitrogen on the pyrazolo ring;
1.7: Formula Ia, 1.1, 1.2, 1.3, 1.4, 1.5 or 1.6 wherein $R_6$ is benzyl;
1.8: Formula Ia, 1.1, 1.2, 1.3, 1.4, 1.5 or 1.6 wherein R is phenylamino or phenylalkylamino (e.g., benzylamino); and/or
1.9: Formula Ia, 1.1, 1.2, 1.3, 1.4, 1.5, 1.6, 1.7, or 1.8 wherein the compounds inhibit phosphodiesterase-mediated (e.g., PDE1-mediated, especially PDE1B-mediated) hydrolysis of cGMP, e.g., with an $IC_{50}$ of less than 1μM, preferably less than 25 nM in an immobilized-metal affinity particle reagent PDE assay, for example, as described in Example 15;

in free or salt form.

In an another embodiment, the Compounds of the Invention are compounds of Formula I wherein
(i) $R_1$ is methyl;
(ii) $R_2$, $R_3$ and $R_4$ are H;
(iii) n=1 and $R_a$ and $R_b$ are, independently, H or methyl;
(iv) $R_5$ is a moiety of Formula A wherein $R_8$, $R_9$, $R_{11}$ and $R_{12}$ are H and $R_{10}$ is phenyl, pyridyl (for example pyrid-2-yl), or thiadiazolyl (e.g., 1,2,3-thiadiazol-4-yl);
(v) $R_6$ is benzyl, phenylamino or benzylamino;
in free or salt form.

In another embodiment, the Compounds of the Invention are compounds of Formula I wherein
(i) $R_1$ is methyl;
(ii) n=0;
(iii) $R_2$ is H and $R_3$ and $R_4$ together form a tri- or tetramethylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
(iv) $R_5$ is a substituted heteroarylmethyl, e.g., para-substituted with haloalkyl; or
$R_5$ is a moiety of Formula A wherein $R_8$, $R_9$, $R_{11}$ and $R_{12}$ are H or halogen and $R_{10}$ is haloalkyl, phenyl, pyridyl (for example pyrid-2-yl), or thiadiazolyl (e.g., 1,2,3-thiadiazol-4-yl); and
(v) $R_6$ is benzyl, phenylamino or benzylamino;
in free or salt form.

In another embodiment, the Compounds of the Invention are compounds of Formula Ia wherein
(i) $R_1$ is methyl;
(ii) $R_2$ is H and $R_3$ and $R_4$ together form a tri- or tetramethylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];
(iii) $R_5$ is a moiety of formula B wherein $R_8$, $R_9$, $R_{11}$, and $R_{12}$ are H and $R_{10}$ is haloalkyl, phenyl, pyridyl (for example pyrid-2-yl), or thiadiazolyl (e.g., 1,2,3-thiadiazol-4-yl); and
(iv) $R_6$ is benzyl, phenylamino or benzylamino;
in free or salt form.

For example, Compounds of the Invention include compounds according to Formulae II, III and IV.

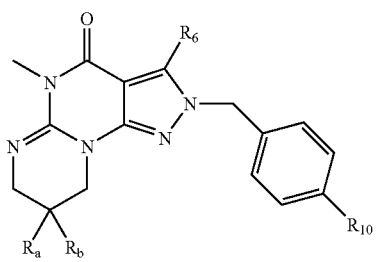

Formula II wherein
$R_a$ and $R_b$ are, independently, H or $C_{1-4}$ alkyl;
$R_6$ is phenylamino or benzylamino;
$R_{10}$ is phenyl, pyridyl (for example pyrid-2-yl), or thiadiazolyl (e.g., 1,2,3-thiadiazol-4-yl);
in free or salt form.

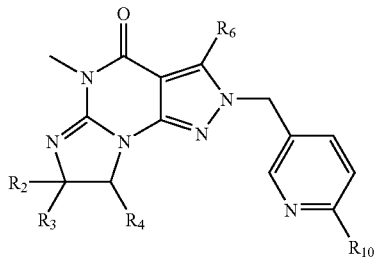

Formula III wherein
- $R_2$ is H and $R_3$ and $R_4$ together form a tri- or tetra-methylene bridge [pref. with the carbons carrying $R_3$ and $R_4$ having the R and S configuration respectively];
- or at least one of $R_2$ and $R_3$ is methyl, isopropyl or arylalkoxy and $R_4$ is H; or $R_2$ and $R_3$ are H and $R_4$ is a $C_{1-4}$ alkyl;
- $R_6$ is phenylamino or benzylamino;
- $R_{10}$ is haloalkyl, phenyl, pyridyl (for example pyrid-2-yl), or thiadiazolyl (e.g., 1,2,3-thiadiazol-4-yl);
- in free or salt form.

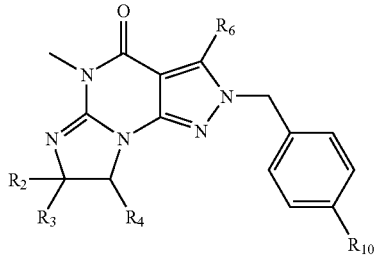

Formula IV wherein
- $R_2$ is H and $R_3$ and $R_4$ together form a tri- or tetra-methylene bridge [pref. with the carbons carrying $R_3$ and $R_4$ having the R and S configuration respectively];
- or at least one of $R_2$ and $R_3$ is methyl, isopropyl or arylalkoxy and $R_4$ is H; or $R_2$ and $R_3$ are H and $R_4$ is a $C_{1-4}$ alkyl;
- $R_6$ is phenylamino or benzylamino;
- $R_{10}$ is phenyl, pyridyl (for example pyrid-2-yl), or thiadiazolyl (e.g., 1,2,3-thiadiazol-4-yl);
- in free or salt form.

Compounds of the Invention include, for example, the title compounds of Examples 1-23 below.

If not otherwise specified or clear from context, the following terms as used herein have the following meetings:

a. "Alkyl" as used herein is a saturated or unsaturated hydrocarbon moiety, preferably saturated, preferably one to four carbon atoms in length, which may be linear or branched, and may be optionally substituted, e.g., mono-, di-, or tri-substituted, e.g., with halogen (e.g., chloro or fluoro), hydroxy, or carboxy.

b. "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy.

c. "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

d. "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

Compounds of the Invention may exist in free or salt form, e.g., as acid addition salts. In this specification unless otherwise indicated language such as Compounds of the Invention is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. For example when the compounds contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. As will be appreciated the term thus embraces conventional pharmaceutical prodrug forms.

The invention also provides methods of making the Compounds of the Invention, novel intermediates useful for making Compounds of the Invention, and methods of using the Compounds of the Invention for treatment of diseases and disorders as set forth below (especially treatment of diseases characterized by reduced dopamine D1 receptor signaling activity, such as Parkinson's disease, restless leg syndrome, depression, and cognitive impairment of schizophrenia).

DETAILED DESCRIPTION OF THE INVENTION

Methods of Making Compounds of the Invention

The compounds of the formula I and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds. All references cited herein are hereby incorporated in their entirety by reference.

Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

Melting points are uncorrected and (dec) indicated decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Terms and Abbreviations:
Bu$^t$OH=tert-butyl alcohol,
CAN=ammonium cerium (IV) nitrate,
DIPEA=diisopropylethylamine,
DMF=N,N-dimethylforamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
K$_2$CO$_3$=potassium carbonate,
MeOH=methanol,
NaHCO$_3$=sodium bicarbonate,
NH$_4$OH=ammonium hydroxide,
PMB=p-methoxybenzyl,
POCl$_3$=phosphorous oxychloride,
SOCl$_2$=thionyl chloride,
TFA=trifluoroacetic acid,
THF=tetrahedrofuran.

The synthetic methods in this invention are illustrated below. The significances for the R groups are as set forth above for formula I unless otherwise indicated.

In an aspect of the invention, intermediate compounds of formula IIb can be synthesized by reacting a compound of formula IIa with a dicarboxylic acid, acetic anhydride and acetic acid mixing with heat for about 3 hours and then cooled:

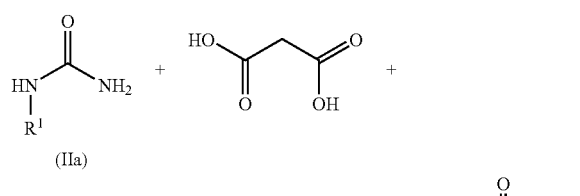

wherein R$^1$ is H or C$_{1-4}$alkyl [e.g., methyl].

Intermediate IIc can be prepared by for example reacting a compound of IIb with for example a chlorinating compound such as POCl$_3$, sometimes with small amounts of water and heated for about 4 hours and then cooled:

Intermediate IId may be formed by reacting a compound of IIc with for example a P$^1$—X in a solvent such as DMF and a base such as K$_2$CO$_3$ at room temperature or with heating:

wherein P$^1$ is a protective group [e.g., p-methoxybenzyl group (PMB)]; X is a leaving group such as a halogen, mesylate, or tosylate.

Intermediate IIe may be prepared by reacting a compound of IId with hydrazine or hydrazine hydrate in a solvent such as methanol and refluxed for about 4 hours and then cooled:

-continued

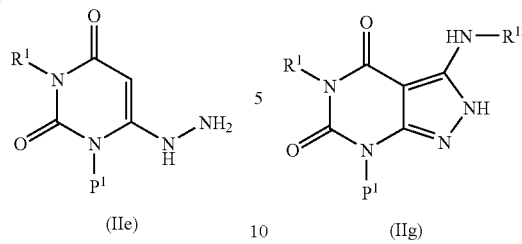

(IIe)

Intermediate IIf can be synthesized by reacting a compound of IIc with hydrazine or hydrazine hydrate in a solvent such as methoxyethanol and refluxed for about 30 min and then cooled:

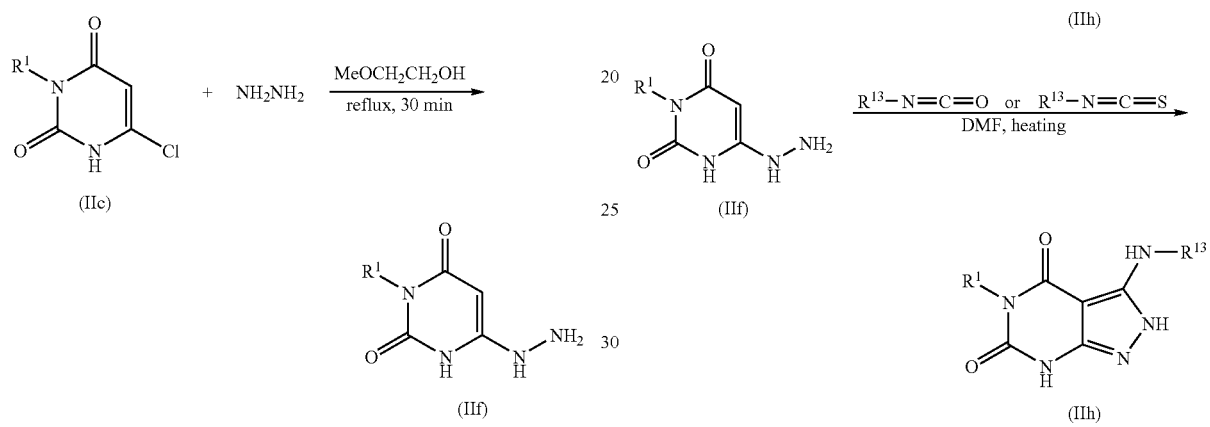

(IIc)　　(IIf)

Intermediate IIg (wherein $R^{13}$ is allyl, aryl [e.g., phenyl], heteroaryl, arylalkyl, or heteroarylalkyl), can be synthesized by reacting a compound of IIe with for example an aryl isothiocyanate or isocyanate in a solvent such as DMF and heated at 110° C. for about 2 days and then cooled:

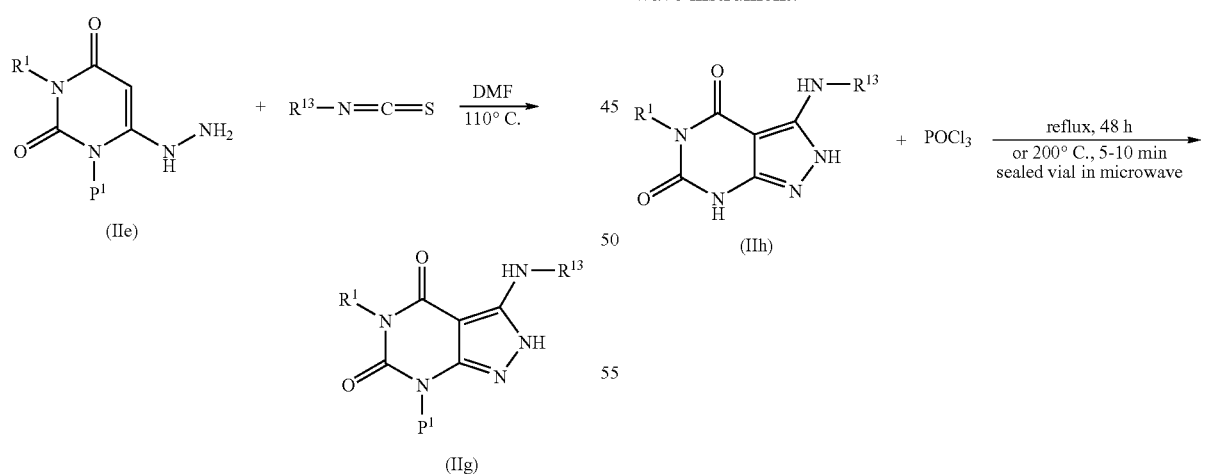

(IIe)　　(IIg)

Intermediate IIh may be synthesized from a compound of IIg by removing the protective group $P^1$ with an appropriate method. For example, if $P^1$ is a p-methoxybenzyl group, then it can be removed with $AlCl_3$ at room temperature or with TFA under heated conditions. Intermediate IIh may also be prepared directly from a compound of IIf using the similar methods, but the yields are relatively low.

(IIg) deprotection →

(IIh)

Intermediate II-I can be prepared by for example reacting a compound of IIh with for example a chlorinating compound such as $POCl_3$. The reaction may be carried out at atmospheric pressure and refluxed for about 2 days, or heated at 150~200° C. for about 10 min in a sealed vial with a microwave instrument.

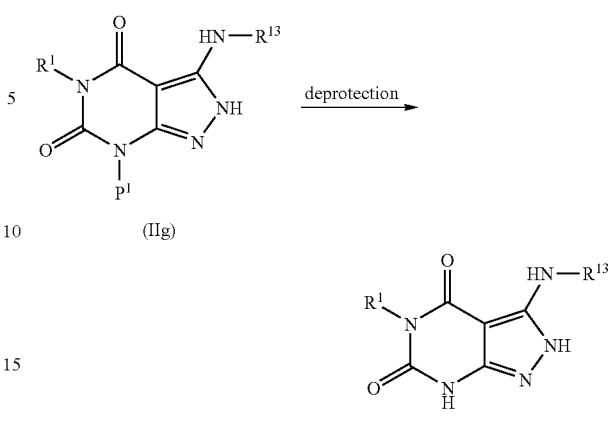

(IIh)

(II-I)

Intermediate IIJ can be prepared by reacting a compound of II-I with an amino alcohol under basic condition in a solvent such as DMF. The reaction may be heated overnight and then cooled:

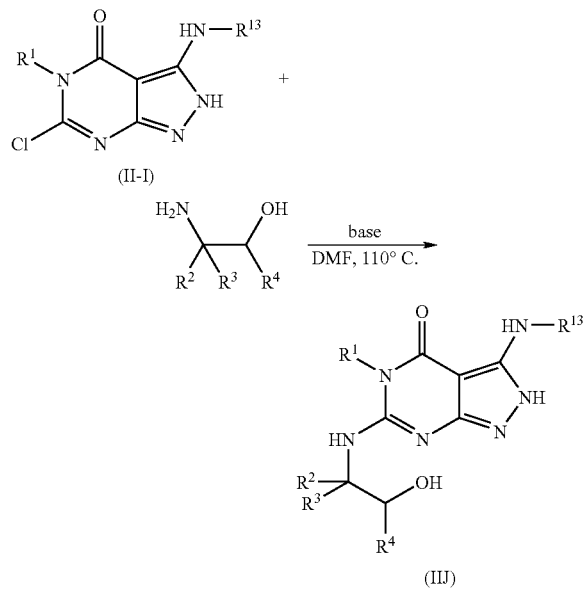

Unless otherwise specified or defined, $R^2$, $R^3$ and $R^4$ are the same as those defined previously, e.g., with respect to Formula I.

Intermediate IIK can be formed by reacting a compound of IIJ with for example a dehydrating agent such as $SOCl_2$ in a solvent such as $CH_2Cl_2$ at room temperature overnight or heated at 35° C. for about 4 hours, and then cooled:

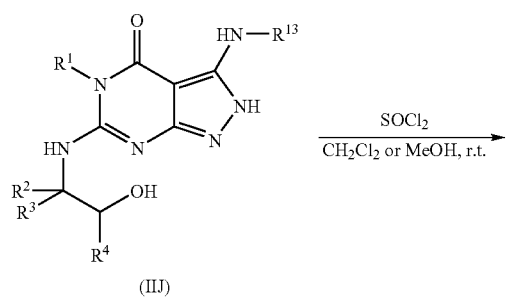

Compound Ia and Ib may be formed by reacting a compound of IIk with for example a $R^5$—X in a solvent such as DMF and a base such as $K_2CO_3$ at room temperature or with heating:

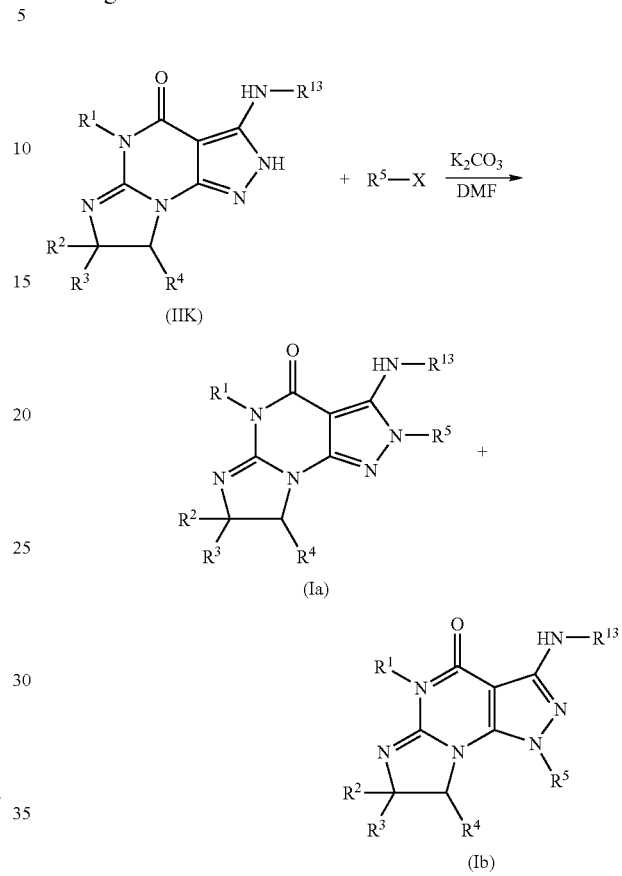

wherein $R^5$ is as defined previously [e.g. an optionally substituted benzyl group]; X is a leaving group such as a halogen, mesylate, or tosylate.

$R^5$ may also be introduced earlier by for example reacting IIg with $R^5X$ and then perform similar procedure as described above to form compound Ia and Ib, as long as $R^5$ will not be cleaved off in the $P^1$ deprotection step.

The second synthetic route is designated for the preparation of compound Ia and Ib wherein $R^6$ is an alkyl, aryl or heteroaryl group.

Intermediate IIIa (wherein $R^7$ is aryl, preferably phenyl substituted with $R_{8-12}$ corresponding to the substituted benzyl of Formula A supra) may be formed by reacting a compound of IIe with an aldehyde $R^7CHO$ in a solvent such as EtOAc at 0° C. or room temperature:

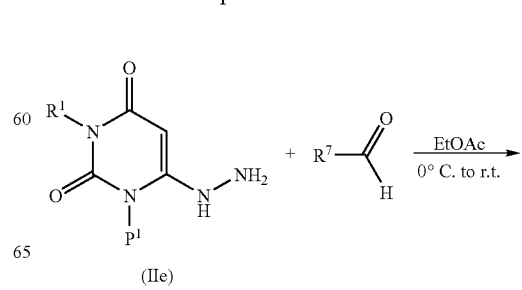

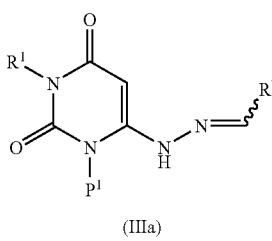

(IIIa)

Intermediate IIIb can be prepared by for example reacting a compound of IIIa with for example an aldehyde in a solvent such as DMF and heated overnight and then cooled:

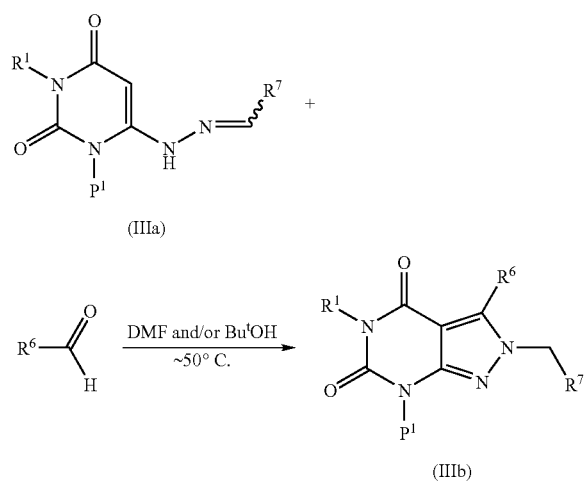

Intermediate IIIc may be synthesized from a compound of IIIb by removing the protective group $P^1$ with an appropriate method. For example, if $P^1$ is a p-methoxybenzyl group, then it can be removed with CAN at room temperature. Intermediate IIIc may also be prepared directly from a compound of IIf using similar methods, but the yields are relatively low.

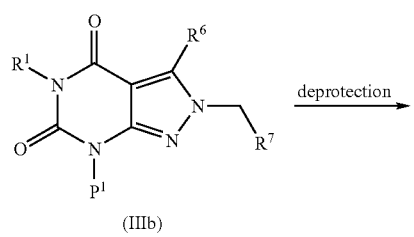

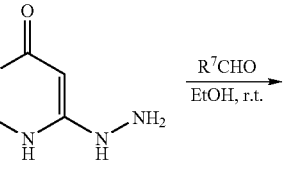

(IIf)

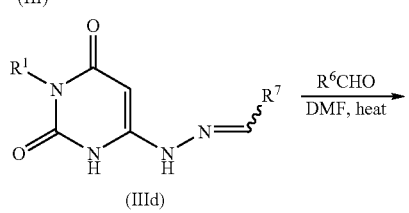

(IIId)

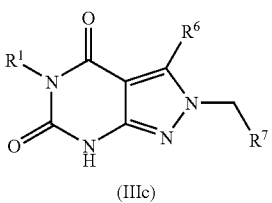

(IIIc)

Intermediate IIIe can be prepared by reacting a compound of IIIc with for example a chlorinating compound such as POCl$_3$. The reaction may be carried out at atmospheric pressure and refluxed for about 2 days, or heated at 150~200° C. for about 10 min in a sealed vial with a microwave instrument.

Intermediate IIIf can be formed by reacting a compound of IIIe with an amino alcohol under basic condition in a solvent such as DMF and heated overnight and then cooled:

-continued

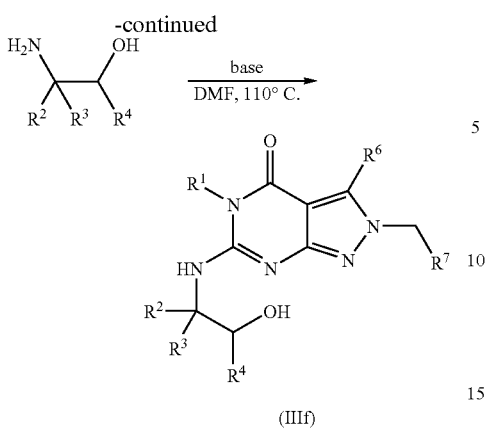

(IIIf)

Compound Ia can be formed by reacting a compound of IIIf with for example a dehydrating agent such as $SOCl_2$ in a solvent such as $CH_2Cl_2$ at room temperature overnight or heated at 35° C. for about 4 hours, and then cooled:

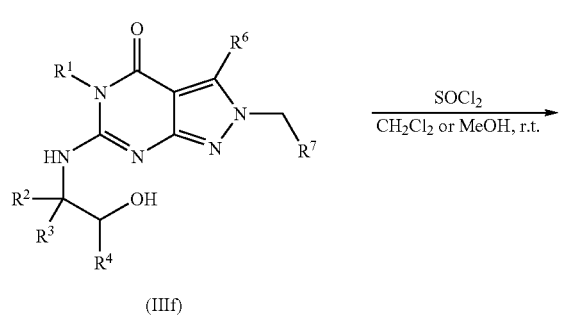

(IIIf)

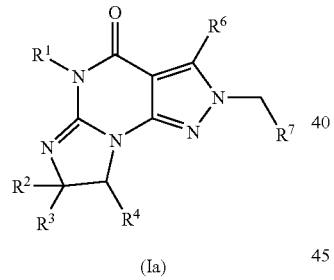

(Ia)

There is an alternative approach for the synthesis of compound Ia and Ib wherein $R^6$ is an alkyl or aryl group. If a harsher condition is employed for the deprotection of IIIb, then the $R^7CH_2$ group can be cleaved off too. For instance, if $P^1$ is a p-methoxybenzyl group and $R^7$ is a substituted phenyl group, then both $P^1$ and $R^7CH_2$ can be cleaved with $AlCl_3$ at room temperature. Thus, Intermediate IIIg may be formed with this approach:

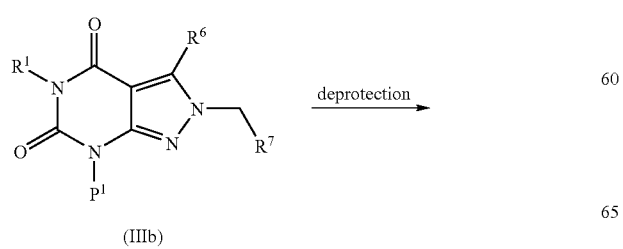

(IIIb)

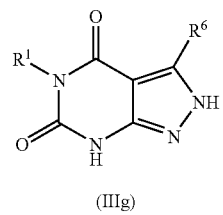

(IIIg)

Intermediate IIIh can be prepared by reacting a compound of IIIg with for example a chlorinating compound such as $POCl_3$. The reaction may be carried out at atmospheric pressure and refluxed for about 2 days, or heated at 150~200° C. for about 10 min in a sealed vial with a microwave instrument.

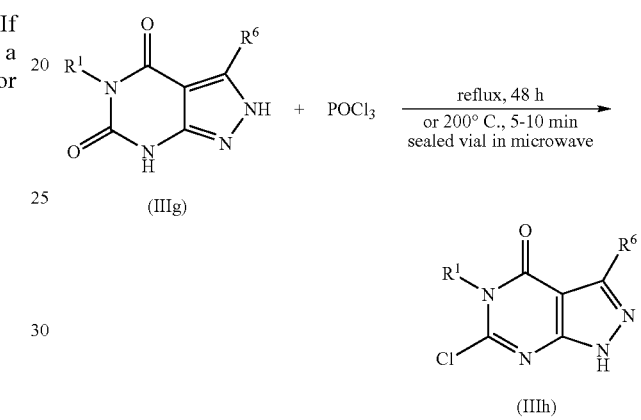

Intermediate III-I can be formed by reacting a compound of IIIh with an amino alcohol under basic condition in a solvent such as DMF and heated overnight and then cooled:

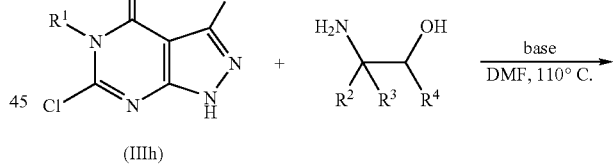

(IIIh)

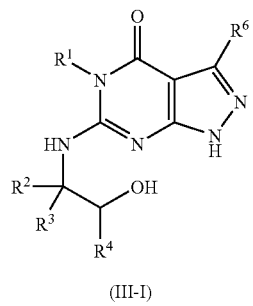

(III-I)

Intermediate IIIJ may be formed by reacting a compound of III-I with for example a dehydrating agent such as SOCl₂ in a solvent such as CH₂Cl₂ or methanol at room temperature overnight or heated at 35° C. for about 4 hours, and then cooled:

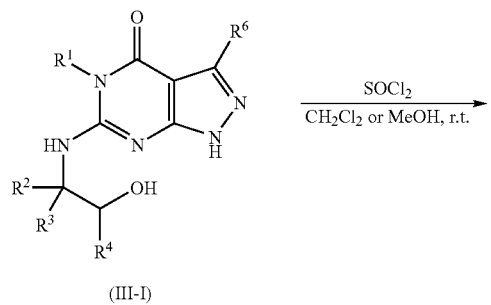

Intermediate IIIJ may also be formed by reacting a compound of Ia with for example a strong acid or Lewis acid such as AlCl₃:

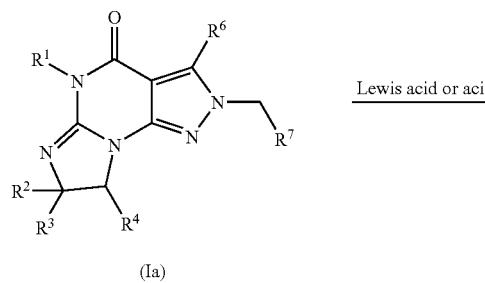

Compound Ia and Ib may be formed by reacting a compound of IIIJ with for example a R⁵—X in a solvent such as DMF and a base such as K₂CO₃ at room temperature or with heating:

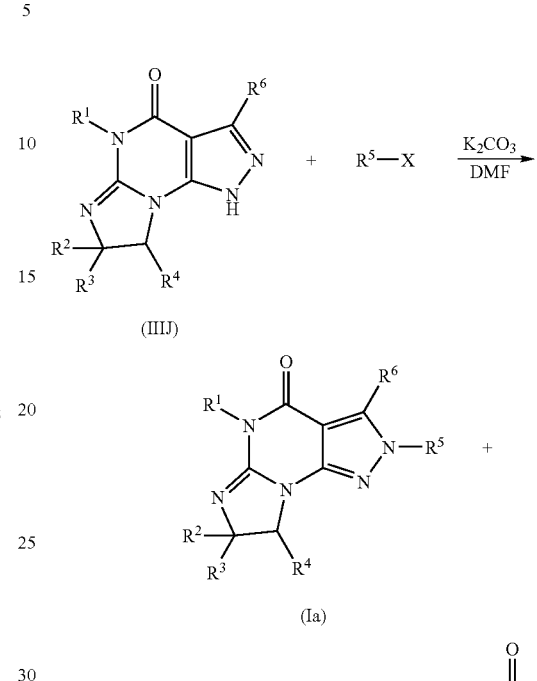

The third synthetic route is designated for the preparation of compound Ia and Ib wherein R⁶ is hydrogen.

Intermediate IVa may be formed by for example reacting a compound of IIe with POCl₃ and DMF:

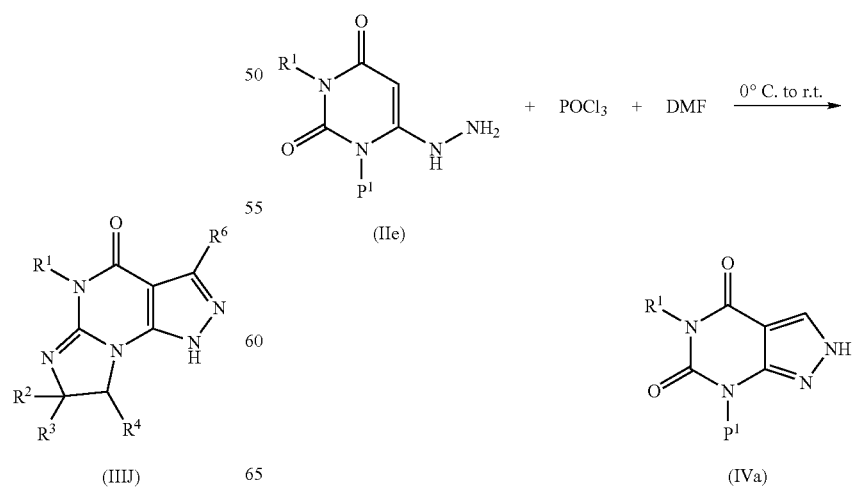

Intermediate IVb may be formed by reacting a compound of IVa with for example a $R^5$—X in a solvent such as DMF and a base such as $K_2CO_3$ at room temperature or with heating:

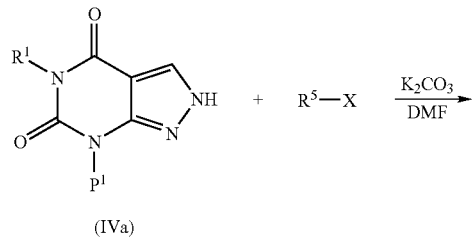

(IVa)

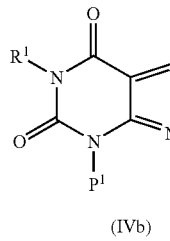

(IVb)

Intermediate IVc may be synthesized from a compound of IVb by removing the protective group $P^1$ with an appropriate method. For example, if $P^1$ is a PMB group, then it can be removed with CAN at room temperature:

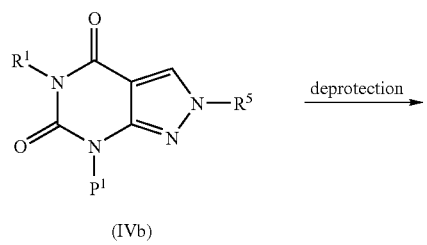

(IVb)

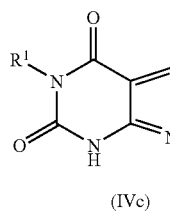

(IVc)

Intermediate IVd can be prepared by reacting a compound of IVc with for example a chlorinating compound such as $POCl_3$ and refluxed for about 2 days, or heated at 150~200° C. for about 10 min in a sealed vial with a microwave instrument and then cooled:

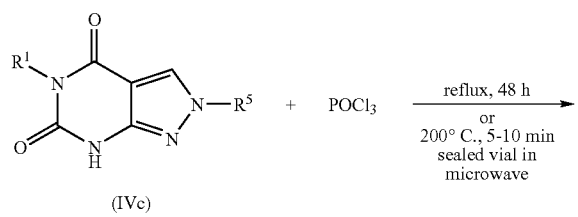

(IVc)

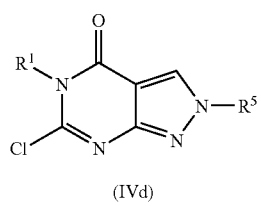

(IVd)

Intermediate IVe can be formed by reacting a compound of IVd with an amino alcohol under basic condition in a solvent such as DMF and heated overnight then cooled:

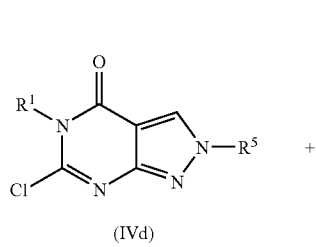

(IVd)

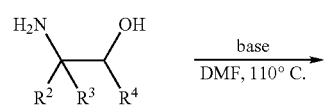

(IVe)

Compound Ia may be formed by reacting a compound of IVe with for example a dehydrating agent such as $SOCl_2$ in a solvent such as $CH_2Cl_2$ at room temperature overnight or heated at 35° C. for about 4 hours, and then cooled. Similar to the methods described above, the $R^5$ group in a compound of Ia can be cleaved off using an appropriate method, and then the obtained intermediate can react with another $R^5X$ to give compound Ia and Ib.

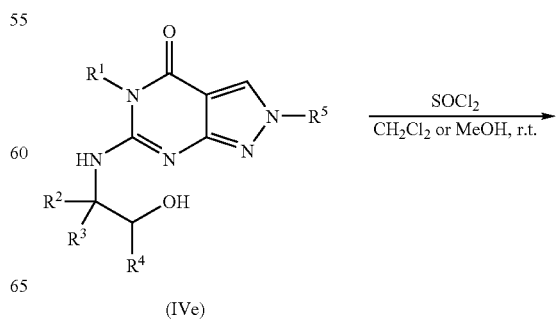

(IVe)

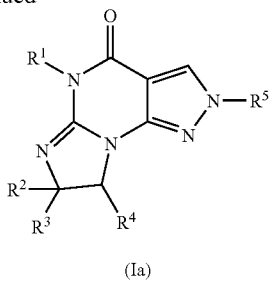

(Ia)

The invention thus provides methods of making Compounds of the Invention as described above, for example, comprising
(i) reacting a 7,8-dihydro-imidazo[1,2-a]pyrazolo[4,3-e]pyrimidin-4(5H)-one or a 7,8,9-trihydro-[1H or 2H]-pyrimido[1,2-a]pyrazolo[4,3-e]pyrimidin-4(5H)-one with a compound of formula X—$R_5$ wherein X is a leaving group, e.g., halogen, mesylate, or tosylate, and $R_5$ is $C_{2-9}$ alkyl, $C_{3-9}$ cycloalkyl, heteroarylalkyl, or substituted arylalkyl, for example wherein $R_5$ is a substituted benzyl of formula A as defined above, e.g., under basic conditions, for example wherein the 7,8-dihydro-imidazo[1,2-a]pyrazolo[4,3-e]pyrimidin-4(5H)-one is a compound of Formula IIIJ:

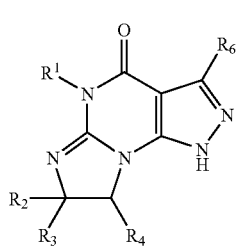

(IIIJ)

wherein $R_{1-6}$ are as defined above, e.g., with reference to Formula I; and/or
(ii) dehydrating a compound of Formula V

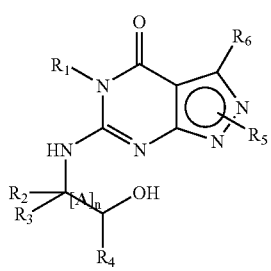

V wherein $R_{1-6}$ and $[A]_n$ are as defined above, e.g., with reference to Formula I, e.g.,
using a dehydrating agent, for example thionyl chloride; and isolating the Compound of the Invention thus obtained.

Methods of Using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1B, thereby increasing intracellular levels of cAMP and cGMP, the Compounds of the Invention potentiate the activity of cyclic nucleotide synthesis inducers.

The invention provides methods of treatment of any one or more of the following conditions:
(i) Neurodegenerative diseases, including Parkinson's disease, restless leg, tremors, dyskinesias, Huntington's disease, Alzheimer's disease, and drug-induced movement disorders;
(ii) Mental disorders, including depression, attention deficit disorder, attention deficit hyperactivity disorder, bipolar illness, anxiety, sleep disorders, cognitive impairment, dementia, psychostimulant withdrawal, and drug addiction;
(iii) Circulatory and cardiovascular disorders, including cerebrovascular disease, stroke, congestive heart disease, hypertension, pulmonary hypertension, and sexual dysfunction;
(iv) Respiratory and inflammatory disorders, including asthma, chronic obstructive pulmonary disease, and allergic rhinitis, as well as autoimmune and inflammatory diseases; and/or
(v) Any disease or condition characterized by low levels of cAMP and/or cGMP (or inhibition of cAMP and/or cGMP signaling pathways) in cells expressing PDE1.
comprising administering an effective amount of a Compound of the Invention to a human or animal patient in need thereof.

The invention also provides a method for enhancing or potentiating dopamine D1 intracellular signaling activity in a cell or tissue comprising contacting said cell or tissue with an amount of a Compound of the Invention sufficient to inhibit PDE1B activity.

The invention also provides a method for treating a PDE1-related, especially PDE1B-related disorder, or a dopamine D1 receptor intracellular signaling pathway disorder, in a patient in need thereof comprising administering to the patient an effective amount of a Compound of the Invention that inhibits PDE1B, wherein PDE1B activity modulates phosphorylation of DARPP-32 and/or the GluR1 AMPA receptor.

The present invention also provides
(i) a Compound of the Invention for use as a pharmaceutical, for example for use in any method or in the treatment of any disease or condition as hereinbefore set forth,
(ii) the use of a Compound of the Invention in the manufacture of a medicament for treating any disease or condition as hereinbefore set forth, and
(iii) a pharmaceutical composition comprising a Compound of the Invention in combination or association with a pharmaceutically acceptable diluent or carrier.

The words "treatment" and "treating" are to be understood accordingly as embracing treatment or amelioration of symptoms of disease as well as treatment of the cause of the disease.

Compounds of the Invention are in particular useful for the treatment of Parkinson's disease.

Compounds of the Invention may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

Example 1

2-(Biphenyl-4-ylmethyl)-7,8-dihydro-5,7,7-trimethyl-[2H]-imidazo-[1,2-a]pyrazolo[4,3-e]pyrimidin-4(5H)-one

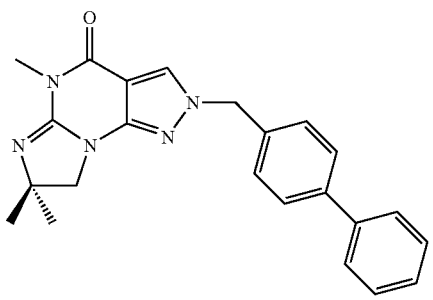

(a) 1-Methylpyrimidine-2,4,6(1H,3H,5H)-trione

To a solution of malonic acid (80 g, 0.79 mol) and methylurea (50 g, 0.68 mol) in 180 ml of acetic acid at 70° C., acetic anhydride (130 ml, 1.37 mol) is added slowly. After the completion of the addition, the reaction mixture is stirred at 90° C. for 3 hours, and then cooled to room temperature. The solvent is removed under reduced pressure, and the residue is treated with 350 mL of ethanol to precipitate out yellowish solid. The solid is recrystallized from ethanol to give 63.1 g product as crystalline solids (Yield: 65.8%). m.p.=131.2-133.1° C. [Lit.[1]: m.p.=130-131.5° C.].

(b) 6-Chloro-3-methylpyrimidine-2,4(1H,3H)-dione

Water (2.7 mL) is added dropwise to a suspension of 1-methylpyrimidine-2,4,6(1H,3H,5H)-trione (14.2 g, 100 mol) in POCl$_3$ (95 mL) at 0° C. The reaction mixture is then heated at 80° C. for 5 hours. The resulting brownish solution is cooled, and POCl$_3$ is evaporated under reduced pressure. The residue is treated with MeOH, and the obtained solid is recrystallized from ethanol to give 11.5 g product (Yield: 71.6%). m.p.=279-282° C. (dec) [Lit.[2]: 280-282° C.]. $^1$H NMR (400 MHz, DMSO-d$_6$) δ 3.10 (S, 3H), 5.90 (S, 1H), 12.4 (br, 1H).

(c) 6-Chloro-1-(4-methoxybenzyl)-3-methylpyrimidine-2,4(1H,3H)-dione

A mixture of 6-chloro-3-methylpyrimidine-2,4(1H,3H)-dione (16.2 g, 101 mmol), p-methoxybenzyl chloride (16.5 mL, 122 mmol) and potassium carbonate (7.0 g, 50.7 mmol) in anhydrous DMF (200 mL) is heated at 60° C. for 3 hours. Additional potassium carbonate (3.0 g, 21.7 mmol) is added, and the reaction mixture heated at 60° C. for another 3 hours. After hot filtration, the filtrate is evaporated to dryness under reduced pressure. The obtained oil is directly used for the synthesis in the next step. A small amount of product is further purified by silica-gel flash chromatography to give pure product as crystals. $^1$H NMR (400 MHz, MeOH-d$_4$) δ 3.37 (s, 3H), 3.83 (s, 3H), 5.24 (s, 2H), 5.96 (s, 1H), 6.91 and 7.32 (AB, 4H, J=6.8 Hz). MS (FAB) m/z 281.23 [M+H]$^+$.

(d) 6-Hydrazinyl-1-(4-methoxybenzyl)-3-methylpyrimidine-2,4(1H,3H)-dione

To a solution of 6-chloro-1-(4-methoxybenzyl)-3-methylpyrimidine-2,4(1H,3H)-dione (2.4 g 8.6 mmol) in EtOH (25 mL) and MeOH (50 mL), anhydrous hydrazine (1.2 mL) is added slowly. The reaction mixture is refluxed for three hours, and then cooled. A large amount of ether is added into the reaction mixture, and then filtered to give 2.0 g of product as crystalline solids (Yield: 84%). $^1$H NMR (DMSO-d$_6$) δ 3.13 (s, 3H), 3.73 (s, 3H), 4.42 (br, 1H), 5.03 (s, 2H), 5.15 (s, 1H), 6.88 and 7.15 (AB, 4H, J=6.4 Hz), 8.08 (br, 1H). MS (FAB) m/z 277.28 [M+H]$^+$.

(e) 7-(4-Methoxybenzyl)-5-methyl-1H-pyrazolo[3,4-d]pyrimidine-4,6(5H,7H)-dione

To a solution of 6-hydrazinyl-1-(4-methoxybenzyl)-3-methylpyrimidine-2,4(1H,3H)-dione (0.45 g, 1.6 mmol) in DMF (2 mL), POCl$_3$ (0.3 mL, 3.3 mmol) is added dropwise at 0° C. After the reaction mixture is stirred at 0° C. for 1 hour, the mixture is treated with methanol carefully to give white solid. The solid is further purified by chromatography to give 0.4 g product (Yield: 85%). $^1$H NMR (DMSO-d$_6$) δ 3.23 (s, 3H), 3.71 (s, 3H), 5.05 (s, 2H), 6.85 and 7.31 (AB, 4H, J=11.6 Hz), 8.47 (s, 1H), 13.5 (br, 1H). MS (FAB) m/z 287.21 [M+H]$^+$.

(f) 2-(Biphenyl-4-ylmethyl)-7-(4-methoxybenzyl)-5-methyl-2H-pyrazolo[3,4-d]pyrimidine-4,6(5H,7H)-dione A mixture of 7-(4-methoxybenzyl)-5-methyl-1H-pyrazolo[3,4-d]pyrimidine-4,6(5H,7H)-dione (0.312 g, 1.09 mmol), p-biphenylmethyl bromide (0.296 g, 1.20 mmol) and potassium carbonate (0.151 g, 1.09 mmol) in acetone (20 mL) is stirred at room temperature overnight. The solvent is evaporated under reduced pressure. The residue is directly purified by chromatography to give 0.382 g product as white solids (Yield: 77.5). $^1$H NMR (400 MHz, CDCl$_3$) δ 3.37 (s, 3H), 3.75 (s, 3H), 5.15 (s, 2H), 5.34 (s, 2H), 6.81 (m, 2H), 7.27 (m, 3H), 7.47 (m, 4H), 7.60 (m, 4H), 7.87 (s, 1H). MS (FAB) m/z 453.3 [M+H]$^+$.

(g) 2-(Biphenyl-4-ylmethyl)-5-methyl-2H-pyrazolo [3,4-d]pyrimidine-4,6(5H,7H)-dione To a solution of 2-(biphenyl-4-ylmethyl)-7-(4-methoxybenzyl)-5-methyl-2H-pyrazolo[3,4-d]pyrimidine-4,6(5H,7H)-dione (300 mg, 0.663 mmol) in THF (9 mL), a solution of ammonium cerium (IV) nitrate (1.82 g, 3.32 mmol) in water (3 mL) is added. The resulting orange solution is stirred at room temperature overnight. Another batch of CAN (1.82 g, 3.32 mmol) is added and the mixture is stirred for 6 hours, and then the third batch of CAN (1.82 g) is added, and the mixture is stirred at r.t. overnight. The reaction mixture is evaporated to dryness. The residue is treated with brine, and extracted with methylene chloride five times. The organic phase is combined and concentrated. The residue is purified by chromatography to give product as white solids with a high yield. $^1$H NMR (400 MHz, DMDO-$d_6$) δ 3.16 (s, 3H), 5.37 (s, 2H), 7.38 (m, 3H), 7.46 (m, 2H), 7.65 (m, 4H), 8.59 (s, 1H), 11.6 (s, 1H). MS (FAB) m/z 333.3 [M+H]$^+$.

(h) 2-(Biphenyl-4-ylmethyl)-6-chloro-5-methyl-2H-pyrazolo[3,4-d]pyrimidin-4(5H)-one 2-(biphenyl-4-ylmethyl)-5-methyl-2H-pyrazolo[3,4-d]pyrimidine-4,6(5H,7H)-dione (25 mg, 0.075 mmol) is refluxed in POCl$_3$ (10 mL) for 60 hours, and the mixture is evaporated to dryness. The residue is purified by silica gel flash chromatography to give 26 mg product as white solids (Yield: 98.5%). $^1$H NMR (400 MHz, CDCl$_3$) δ 3.68 (s, 3H), 5.45 (s, 2H), 7.39 (m, 3H), 7.43 (m, 2H), 7.59 (m, 4H), 8.01 (s, 1H). MS (FAB) m/z 351.2 [M+H]$^+$.

(i) 2-(Biphenyl-4-ylmethyl)-6-(1-hydroxy-2-methyl-propan-2-ylamino)-5-methyl-2H-pyrazolo[3,4-d]pyrimidin-4(5H)-one A solution of 2-(biphenyl-4-ylmethyl)-6-chloro-5-methyl-2H-pyrazolo[3,4-d]pyrimidin-4(5H)-one (26 mg, 0.074 mmol) and 2-amino-2-methyl-1-propanol (71 µL, 0.74 mmol) in DMF (1 mL) is heated at 110° C. overnight. The reaction mixture is then purified by chromatography to give 21.1 mg product (Yield: 71%). MS (FAB) m/z 404.2 [M+H]$^+$.

(j) 2-(Biphenyl-4-ylmethyl)-7,8-dihydro-5,7,7-trimethyl-[2H]-imidazo-[1,2-a]pyrazolo[4,3-e]pyrimidin-4(5H)-one To a solution of 2-(biphenyl-4-ylmethyl)-6-(1-hydroxy-2-methylpropan-2-ylamino)-5-methyl-2H-pyrazolo[3,4-d]pyrimidin-4(5H)-one (17 mg, 0.042 mmol) in methylene chloride (1 mL), is added 2.0 M CH$_2$Cl$_2$ solution of thionyl chloride (63 µL, 0.126 mmol) under argon. The reaction mixture is stirred at r.t. overnight. The reaction is quenched with 5% NaHCO$_3$, and the resulting mixture is purified by chromatography to give 11 mg of the final product as white solids (Yield: 68%). $^1$H NMR (400 MHz, DMSO-$d_6$+CDCl$_3$) δ 1.36 (s, 6H), 3.30 (s, 3H), 3.69 (s, 2H), 5.30 (s, 2H), 7.36 (m, 3H), 7.43 (m, 2H), 7.58 (m, 4H), 8.10 (s, 1H). MS (FAB) m/z 386.1 [M+H]$^+$.

Example 2

Cis-(6aR*,10aS*)-1-(4-Benzoylbenzyl)-5,6a,7,8,9,10,10a-heptahydro-5-methyl-3-(phenylamino)cyclohex[4,5]imidazo[1,2-a]pyrazolo[4,3-e]pyrimidin-4(1H)-one

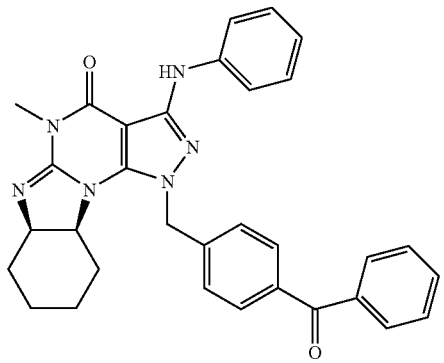

(a) 7-(4-Methoxybenzyl)-5-methyl-3-(phenylamino)-1H-pyrazolo[3,4-d]pyrimidine-4,6(5H,7H)-dione Phenyl isothiocyanate (3.9 mL, 32.7 mmol) is added to a suspension of 6-hydrazinyl-1-(4-methoxybenzyl)-3-methylpyrimidine-2,4(1H,3H)-dione (0.45 g, 1.6 mmol) in DMF (12 mL). The reaction mixture is heated at 120° C. for 40 hours, and then evaporated to remove solvent under reduced pressure. The residue is washed with hexanes, and then treated with MeOH (125 mL), and stored at −15° C. for 2 days to give a crystalline solid. The solid is recrystallized from CH$_3$OH-EtOAc to afford 2.5 g product (Yield: 61%). $^1$H NMR (400 MHz, DMSO-$d_6$) δ 3.21 (s, 3H), 3.73 (s, 3H), 5.01 (s, 2H), 6.88-7.36 (m, 9H). MS (FAB) m/z 378.3 [M+H]$^+$.

(b) 5-Methyl-3-(phenylamino)-1H-pyrazolo[3,4-d]pyrimidine-4,6(5H,7H)-dione

AlCl$_3$ (0.733 g, 5.50 mmol) is added to a solution of 7-(4-methoxybenzyl)-5-methyl-3-(phenylamino)-1H-pyrazolo[3,4-d]pyrimidine-4,6(5H,7H)-dione (0.692 g, 1.83 mmol) and anisole (40 µL, 0.367 mmol) in 1,2-dichloroethane (10 mL) under argon. The reaction mixture is stirred at room temperature for 30 min, and then quenched with water with cooling. The resulting suspension is filtered through a layer of celite and the celite is washed with MeOH (20 mL). The product is eluted from the celite with a large amount of THF. The THF eluent is evaporated to afford 0.47 g of product (Yield: 99%). MS (FAB) m/z 258.2 [M+H]$^+$.

(c) 6-Chloro-5-methyl-3-(phenylamino)-1H-pyrazolo[3,4-d]pyrimidin-4(5H)-one 5-methyl-3-(phenylamino)-1H-pyrazolo[3,4-d]pyrimidine-4,6(5H,7H)-dione (450 mg, 1.75 mmol) is refluxed in POCl$_3$ (20 mL) for 60 hours, and the mixture is evaporated to dryness. The residue is purified by silica gel flash chromatography to give 122 mg product as white solids and 207 mg starting material is recovered (Yield: 47%). MS (FAB) m/z 276.1 [M+H]$^+$.

(d) 6-((1R*,2R*)-2-Hydroxycyclohexylamino)-5-methyl-3-(phenylamino)-1H-pyrazolo[3,4-d]pyrimidin-4(5H)-one A solution of 6-chloro-5-methyl-3-(phenylamino)-1H-pyrazolo[3,4-d]pyrimidin-4(5H)-one (75.8 mg, 0.275 mmol), trans-2-amino-cyclohexanol hydrochloride (83.4 mg, 0.55 mmol) and DIPEA (144 µL, 0.825 mmol) in DMF (3 mL) is heated at 110° C. overnight. The reaction mixture is evaporated to remove DMF under reduced pressure. The residue is then purified by chromatography to give 63.1 mg product (Yield: 64.7%). MS (ESI) m/z 355.0 [M+H]$^+$.

(e) Cis-(6aR*,10aS*)-5,6a,7,8,9,10,10a-heptahydro-5-methyl-3-(phenylamino)cyclohex[4,5]imidazo[1,2-a]pyrazolo[4,3-e]pyrimidin-4(1H)-one 2.0 M solution of thionyl chloride in $CH_2Cl_2$ (267 µL, 0.534 mmol) is added to a solution of 6-((1R*,2R*)-2-hydroxycyclohexylamino)-5-methyl-3-(phenylamino)-1H-pyrazolo[3,4-d]pyrimidin-4(5H)-one (63.1 mg, 0.178 mmol) in $CH_2Cl_2$ (6 mL) and THF (4 mL). The reaction mixture is stirred at r.t. overnight, and then quenched with 100 µL of 28% $NH_4OH$. The resulting mixture is concentrated and purified by chromatography to give 25 mg product as white solids (Yield: 42%). MS (ESI) m/z 337.1 [M+H]$^+$.

(f) Cis-(6aR*,10aS*)-1-(4-Benzoylbenzyl)-5,6a,7,8,9,10,10a-heptahydro-5-methyl-3-(phenylamino)cyclohex[4,5]imidazo[1,2-a]pyrazolo[4,3-e]pyrimidin-4(1H)-one A mixture of Cis-(6aR*,10aS*)-5,6a,7,8,9,10,10a-heptahydro-5-methyl-3-(phenylamino)cyclohex[4,5]imidazo[1,2-a]pyrazolo[4,3-e]pyrimidin-4(1H)-one (7.1 mg, 0.021 mmol), 4-benzoylbenzyl bromide (5.8 mg, 0.021 mmol), and $K_2CO_3$ (2.92 mg, 0.021 mmol) in DMF (1 mL) is stirred at room temperature overnight under argon. The reaction mixture is purified by a semi-preparative HPLC to give 3.5 mg of the final product (Yield: 31%). MS (ESI) m/z 531.1 [M+H]$^+$.

Example 3

3-Benzyl-2-(biphenyl-4-ylmethyl)-7,8-dihydro-5,7,7-trimethyl-[2H]-imidazo-[1,2-a]pyrazolo[4,3-e]pyrimidin-4(5H)-one

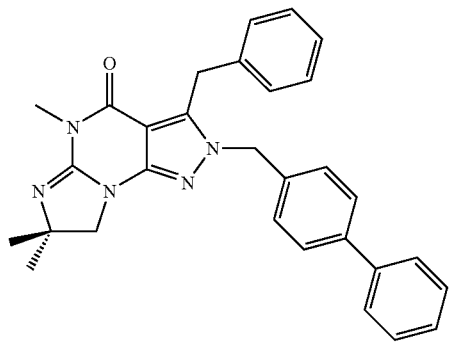

(a) 6-(2-(Biphenyl-4-ylmethylene)hydrazinyl)-1-(4-methoxybenzyl)-3-methylpyrimidine-2,4(1H,3H)-dione A solution of 4-phenylbenzaldehyde (395 mg, 2.17 mmol) in EtOAc is slowly added into a dry ice cooled slurry of 6-hydrazinyl-1-(4-methoxybenzyl)-3-methylpyrimidine-2,4(1H,3H)-dione (200 mg, 0.724 mmol) in EtOAc. After the addition, the reaction mixture is stirred at room temperature for 2 hours. The solvent is evaporated under reduced pressure, and the residue is triturated with MeOH, followed by filtration to give 256 mg product as pale yellow solids (Yield: 80.3%). $^1$H NMR (400 MHz, DMSO-$d_6$) δ 3.17 (s, 3H), 3.71 (s, 3H), 5.22 (s, 2H), 5.59 (s, 1H), 6.91 and 7.21 (AB, J=7.2 Hz, 4H), 7.37-7.81 (m, 9H), 8.36 (s, 1H), 10.67 (s, 1H). MS (FAB) m/z 441.4 [M+H]$^+$.

(b) 3-Benzyl-2-(biphenyl-4-ylmethyl)-7-(4-methoxybenzyl)-5-methyl-2H-pyrazolo[3,4-d]pyrimidine-4,6(5H,7H)-dione Acetic acid (4.4 mL) is added in to a solution of 6-(2-(Biphenyl-4-ylmethylene)hydrazinyl)-1-(4-methoxybenzyl)-3-methylpyrimidine-2,4(1H,3H)-dione (3.2 g, 7.26 mmol) in DMF (50 mL) and Bu$^t$OH (25 mL) at 50° C. Piperidine (8.7 mL) is mixed with a solution of 2-phenylacetaldehyde (8.5 mL, 72.6 mmol) in DMF (20 mL), and the resulting greenish solution is added in to the above solution. The reaction mixture is stirred at 40-45° C. for 36 hours under argon, and the solvent is evaporated under high vacuum. The residue is treated with MeOH (200 mL) to precipitate out 1.23 g product as sandy solids (Yield: 31.4%). MS (FAB) m/z 543.4 [M+H]$^+$.

(c) 3-Benzyl-2-(biphenyl-4-ylmethyl)-5-methyl-2H-pyrazolo[3,4-d]pyrimidine-4,6(5H,7H)-dione A solution of ammonium cerium (IV) nitrate (204 mg, 0.371 mmol) in water (0.6 mL) is added to a solution of 3-benzyl-2-(biphenyl-4-ylmethyl)-7-(4-methoxybenzyl)-5-methyl-2H-pyrazolo[3,4-d]pyrimidine-4,6(5H,7H)-dione (40.3 mg, 0.0743 mmol) in THF (2 mL). The resulting orange solution is stirred at room temperature overnight. Another batch of CAN (204 mg, 0.371 mmol) is added and the mixture is stirred for 3 hours, and then the third batch of CAN (204 mg) is added, and the mixture is stirred at r.t. overnight. The reaction mixture is evaporated to dryness. The residue is treated with brine, and extracted with methylene chloride five times. The organic phase is combined and concentrated. The residue is purified by chromatography to give 11.6 mg product as white solids (Yield: 36.9%). $^1$H NMR (400 MHz, acetone-$d_6$) δ 3.27 (s, 3H), 4.51 (s, 2H), 5.33 (s, 2H), 7.13-7.62 (m, 14H), 10.26 (s, 1H). MS (FAB) m/z 423.2 [M+H]$^+$.

(d) 3-Benzyl-2-(biphenyl-4-ylmethyl)-6-chloro-5-methyl-2H-pyrazolo[3,4-d]pyrimidin-4(5H)-one 3-benzyl-2-(biphenyl-4-ylmethyl)-5-methyl-2H-pyrazolo[3,4-d]pyrimidine-4,6(5H,7H)-dione (10 mg, 0.024 mmol) is refluxed in $POCl_3$ (10 mL) for 4 days, and then the mixture is evaporated to dryness. The residue is purified by silica gel flash chromatography to give 10.4 mg product as white solids (Yield: 100%). MS (FAB) m/z 441.2 [M+H]$^+$.

(e) 3-Benzyl-2-(biphenyl-4-ylmethyl)-6-(1-hydroxy-2-methylpropan-2-ylimino)-5-methyl-6,7-dihydro-2H-pyrazolo[3,4-d]pyrimidin-4(5H)-one A solution of 3-Benzyl-2-(biphenyl-4-ylmethyl)-6-chloro-5-methyl-2H-pyrazolo[3,4-d]pyrimidin-4(5H)-one (9.5 mg, 0.022 mmol) and 2-amino-2-methyl-1-propanol (21 μL, 0.22 mmol) in DMF (2 mL) is heated at 110° C. overnight. The reaction mixture is then purified by chromatography to give 5.5 mg product (Yield: 52%). MS (FAB) m/z 494.4 [M+H]$^+$.

(f) 3-Benzyl-2-(biphenyl-4-ylmethyl)-7,8-dihydro-5,7,7-trimethyl-[2H]-imidazo-[1,2-a]pyrazolo[4,3-e]pyrimidin-4(5H)-one A 2.0 M solution of thionyl chloride (25 μL, 0.050 mmol) in CH$_2$Cl$_2$ is added into a solution of 3-benzyl-2-(biphenyl-4-ylmethyl)-6-(1-hydroxy-2-methylpropan-2-ylimino)-5-methyl-6,7-dihydro-2H-pyrazolo[3,4-d]pyrimidin-4(51)-one (5.0 mg, 0.010 mmol) in methylene chloride (1 mL). The reaction mixture is stirred at r.t. overnight, and then quenched with 5% NaHCO$_3$. The resulting mixture is purified by chromatography to give 3.2 mg of the final product (Yield: 67%). MS (FAB) m/z 476.4 [M+H]$^+$.

Example 4

1-(Biphenyl-4-ylmethyl)-7,8-dihydro-5,7,7-trimethyl-3-(phenylamino)-[1H]-imidazo-[1,2-a]pyrazolo[4,3-e]pyrimidin-4(5H)-one

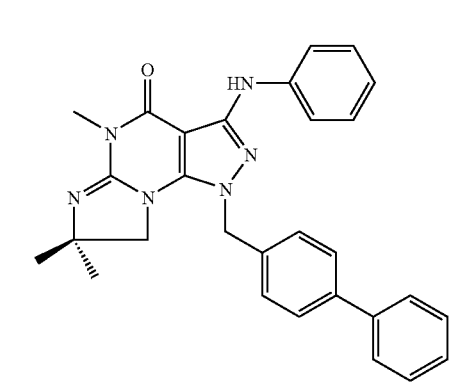

The synthesis method is analogous to example 2 wherein 2-amino-2-methyl-1-propanol is added in step (d) instead of trans-2-amino-cyclohexanol hydrochloride; and p-biphenyl-methyl bromide is added in step (f) instead of benzoylbenzyl bromide.

Example 5

1-(4-(1,2,3-thiadiazol-4-yl)benzyl)-7,8-dihydro-5,7,7-trimethyl-3-(phenylamino)-[1H]-imidazo-[1,2-a]pyrazolo[4,3-e]pyrimidin-4(5H)-one

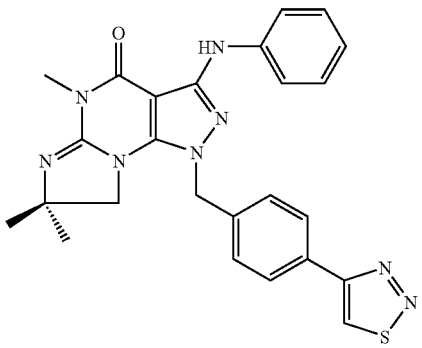

The synthesis method is analogous to example 2 wherein 2-amino-2-methyl-1-propanol is added in step (d) instead of trans-2-amino-cyclohexanol hydrochloride; and 4-(1,2,3-thiadiazol-4yl)benzyl bromide is added in step (f) instead of benzoylbenzyl bromide.

Example 6

1-(Biphenyl-4-ylmethyl)-3-((biphenyl-4-ylmethyl)(phenyl)amino)-7,8-dihydro-5,7,7-trimethyl-[1H]-imidazo-[1,2-a]pyrazolo[4,3-e]pyrimidin-4(5H)-one

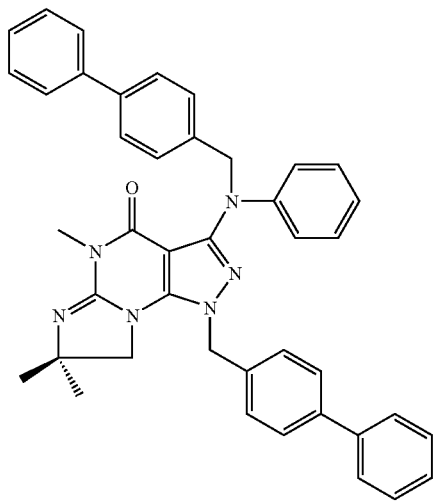

The synthesis method is analogous to example 2 wherein 2-amino-2-methyl-1-propanol is added in step (d) instead of trans-2-amino-cyclohexanol hydrochloride; and p-biphenyl-methyl bromide is added in step (f) instead of benzoylbenzyl bromide.

Example 7

Cis-(6aR*,10aS*)-5,6a,7,8,9,10,10a-heptahydro-5-methyl-3-(phenylamino)-1-(4-(pyridin-2yl)benzyl)-cyclohex[4,5]imidazo[1,2-a]pyrazolo[4,3-e]pyrimidin-4-(1H)-one

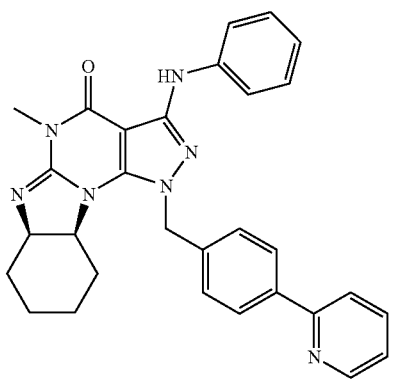

The synthesis method is analogous to example 2 wherein 2-(4-(bromomethyl)phenyl)pyridine is added in step (f) instead of benzoylbenzyl bromide.

Example 8

Cis-(6aR*,10aS*)-2-(4-(Pyridin-2yl)benzyl)-5,6a,7,8,9,10,10a-heptahydro-5-methyl-3-(phenylamino)cyclohex[4,5]imidazo[1,2-a]pyrazolo[4,3-e]pyrimidin-4(2H)-one

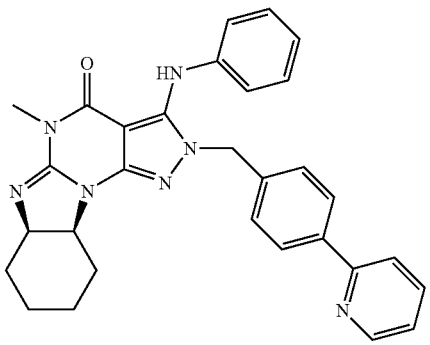

The synthesis method is analogous to example 2 wherein 4-pyrid-2-ylbenzyl bromide is added in step (f) instead of benzoylbenzyl bromide.

Example 9

Cis-(6aR*,10aS*)-3-(Benzyl)-5,6a,7,8,9,10,10a-heptahydro-5-methyl-2-(4-(1,2,3-thiadiazol-4-yl)benzyl)-cyclohex[4,5]imidazo[1,2-a]pyrazolo[4,3-e]pyrimidin-4(2H)-one

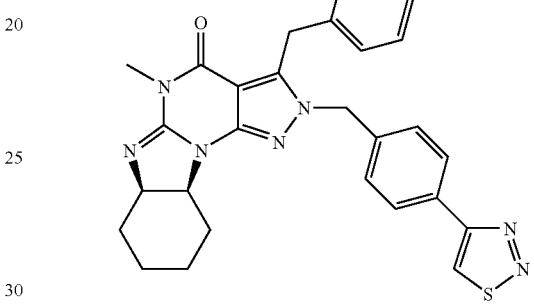

The synthesis method is analogous to example 3 wherein 4-(1,2,3-thiadiazol-4yl)benzaldehyde and DMF is added in step (a) instead of 4-phenylbenzaldehyde and heated overnight; and trans-2-amino-cyclohexanol hydrochloride is added in step (e) instead of 2-amino-2-methyl-1-propanol.

Example 10

Cis-(6aR*,10aS*)-3-(Benzyl)-2-(4-Biphenyl-4-ylmethyl)-5,6a,7,8,9,10,10a-heptahydro-5-methyl-cyclohex[4,5]imidazo[1,2-a]pyrazolo[4,3-e]pyrimidin-4(2H)-one

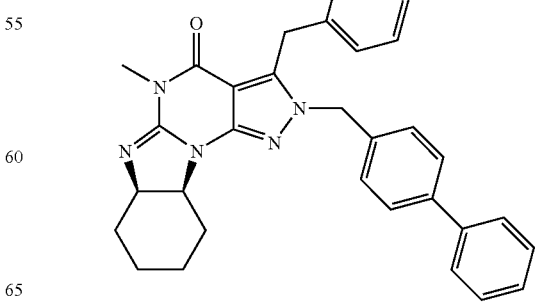

The synthesis method is analogous to example 3 wherein trans-2-amino-cyclohexanol hydrochloride is added in step (e) instead of 2-amino-2-methyl-1-propanol.

Example 11

(R)-3-(Benzyl)-2-(biphenyl-4-ylmethyl)-7,8-dihydro-7-isopropyl-5-methyl-[2H]-imidazo-[1,2-a]pyrazolo[4,3-e]pyrimidin-4(5H)-one

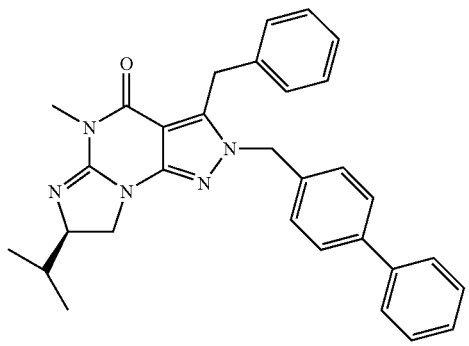

The synthesis method is analogous to example 3 wherein (R)-2-amino-3-methylbutan-1-ol is added in step (e) instead of 2-amino-2-methyl-1-propanol.

Example 12

(6aR,9aS)-5,6a,7,8,9,9a-hexahydro-5-methyl-3-(phenylamino)-2-(4-Pyridin-2yl)-benzyl)-cyclopent[4,5]imidazo[1,2-a]pyrazolo[4,3-e]pyrimidin-4(2H)-one

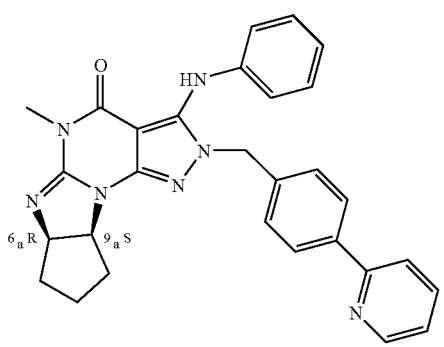

The synthesis method is analogous to example 2 wherein (1R,2R)-2-amino-cyclopentanol is added in step (d) instead of trans-2-amino-cyclohexanol hydrochloride; and 2-(4-(bromomethyl)phenyl)pyridine is added in step (f) instead of benzoylbenzyl bromide.

Example 13

(6aR,9aS)-5,6a,7,8,9,9a-hexahydro-5-methyl-3-(phenylamino)-1-(4-Pyridin-2yl)-benzyl)-cyclopent[4,5]imidazo[1,2-a]pyrazolo[4,3-e]pyrimidin-4(1H)-one

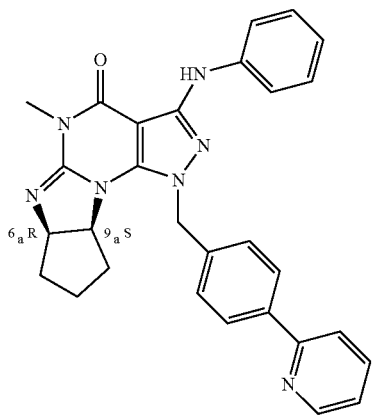

The synthesis method is analogous to example 2 wherein (1R,2R)-2-amino-cyclopentanol is added in step (d) instead of trans-2-amino-cyclohexanol hydrochloride; and 4-pyrid-2-ylbenzyl bromide is added in step (f) instead of benzoylbenzyl bromide.

Example 14

(6aR,9aS)-3-(benzylamino)-5,6a,7,8,9,9a-hexahydro-5-methyl-2-(4-Pyridin-2yl)-benzyl)-cyclopent[4,5]imidazo[1,2-a]pyrazolo[4,3-e]pyrimidin-4(2H)-one

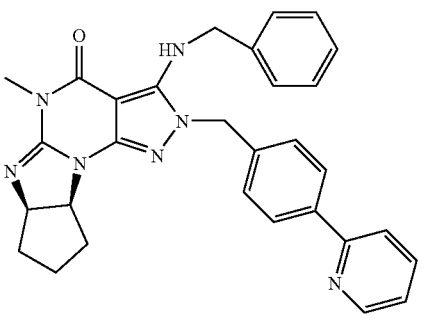

The synthesis method is analogous to example 2 wherein benzyl isothiocyanate is added in step (a) instead of phenyl isothiocyanate; (1R,2R)-2-amino-cyclopentanol is added in step (d) instead of trans-2-amino-cyclohexanol hydrochloride; and 4-pyrid-2-ylbenzyl bromide is added in step (f) instead of benzoylbenzyl bromide.

Example 15

(6aR,9aS)-3-(phenylamino)-5,6a,7,8,9,9a-hexahydro-5-methyl-2-(biphenyl-4-ylmethyl)-cyclopent[4,5]imidazo[1,2-a]pyrazolo[4,3-e]pyrimidin-4(2H)-one

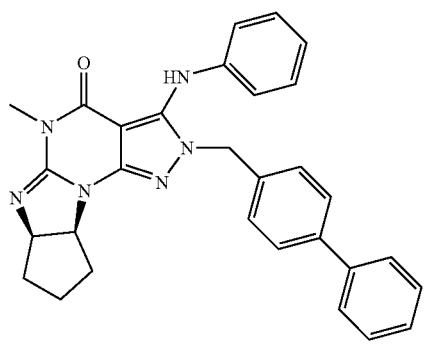

The synthesis method is analogous to example 2 wherein (1R,2R)-2-amino-cyclopentanol is added in step (d) instead of trans-2-amino-cyclohexanol hydrochloride; and 4-(bromomethyl)biphenyl is added in step (f) instead of benzoylbenzyl bromide.

Example 16

2-(Biphenyl-4-ylmethyl)-7,8,9-trihydro-5,8,8-trimethyl-3-(phenylamino)-[2H]-pyrimido-[1,2-a]pyrazolo[4,3-e]pyrimidin-4(5H)-one

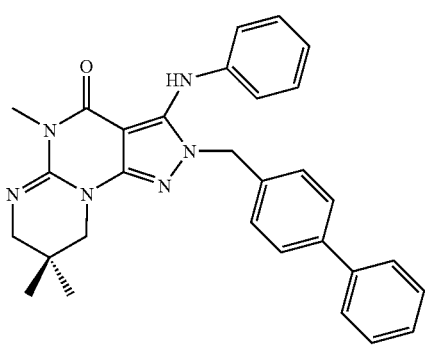

The synthesis method is analogous to example 2 wherein 3-amino-2,2-dimethyl-1-propanol is added in step (d) instead of trans-2-amino-cyclohexanol hydrochloride; and 4-(bromomethyl)biphenyl is added in step (f) instead of benzoylbenzyl bromide.

Example 17

(7R)-2-(Biphenyl-4-ylmethyl)-7,8-dihydro-5,7-dimethyl-3-(phenylamino)-[2H]-imidazo-[1,2-a]pyrazolo[4,3-e]pyrimidin-4(5H)-one

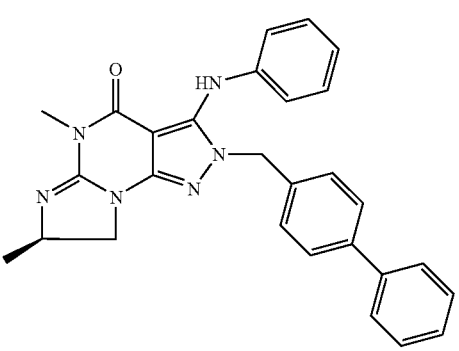

The synthesis method is analogous to example 2 wherein (R)-2-aminoprop-1-ol is added in step (d) instead of trans-2-amino-cyclohexanol hydrochloride; and 4-(bromomethyl)biphenyl is added in step (f) instead of benzoylbenzyl bromide.

Example 18

(8R)-2-(Biphenyl-4-ylmethyl)-7,8-dihydro-5,8-dimethyl-3-(phenylamino)-[2H]-imidazo-[1,2-a]pyrazolo[4,3-e]pyrimidin-4(5H)-one

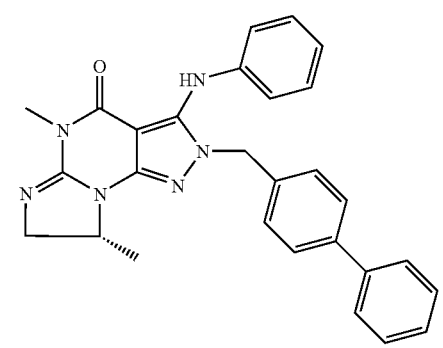

The synthesis method is analogous to example 2 wherein (R)-1-aminopropan-2-ol is added in step (d) instead of trans- 2-amino-cyclohexanol hydrochloride; and 4-(bromomethyl)biphenyl is added in step (f) instead of benzoylbenzyl bromide.

Example 19

(7R)-2-(Biphenyl-4-ylmethyl)-7,8-dihydro-3-(phenylamino)-5-methyl-7-(1-methylethyl)-[2H]-imidazo-[1,2-a]pyrazolo[4,3-e]pyrimidin-4(5H)-one

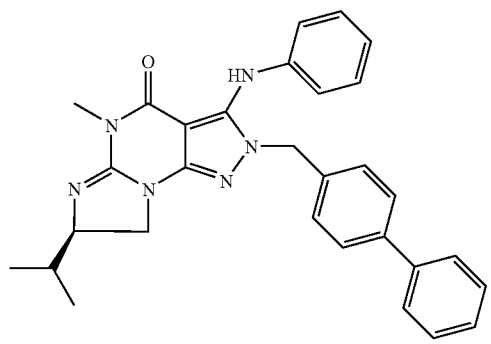

The synthesis method is analogous to example 2 wherein (R)-2-amino-3-methylbutan-1-ol is added in step (d) instead of trans-2-amino-cyclohexanol hydrochloride; and 4-(bromomethyl)biphenyl is added in step (f) instead of benzoylbenzyl bromide.

Example 20

(6aR,9aS)-3-(phenylamino)-5,6a,7,8,9,9a-hexahydro-5-methyl-2-(4-(trifluoromethyl)-benzyl)-cyclopent[4,5]imidazo[1,2-a]pyrazolo[4,3-e]pyrimidin-4(2H)-one

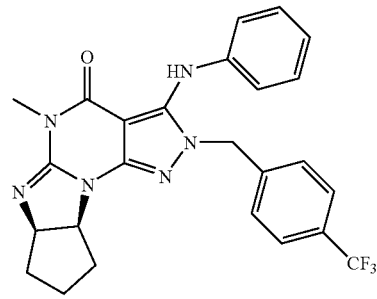

The synthesis method is analogous to example 2 wherein (1R,2R)-2-amino-cyclopentanol is added in step (d) instead of trans-2-amino-cyclohexanol hydrochloride; and p-trifluoromethylbenzyl bromide is added in step (f) instead of benzoylbenzyl bromide.

Example 21

(6aR,9aS)-3-(phenylamino)-5,6a,7,8,9,9a-hexahydro-5-methyl-2-((6-trifluoromethyl)-pyridin-3-yl)methyl)-cyclopent[4,5]imidazo[1,2-a]pyrazolo[4,3-e]pyrimidin-4(2H)-one

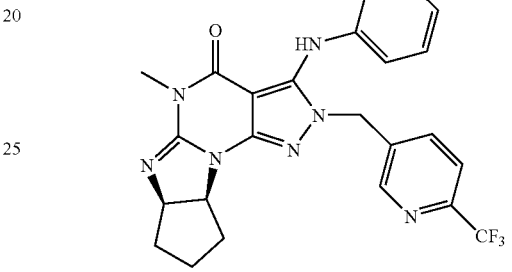

The synthesis method is analogous to example 2 wherein (1R,2R)-2-amino-cyclopentanol is added in step (d) instead of trans-2-amino-cyclohexanol hydrochloride; and 5-(bromomethyl)-2-(trifluoromethyl)pyridine is added in step (f) instead of benzoylbenzyl bromide.

Example 22

(6aR,9aS)-3-(phenylamino)-5,6a,7,8,9,9a-hexahydro-5-methyl-2-(3-fluoro-4-(trifluoromethyl)-benzyl)-cyclopent[4,5]imidazo[1,2-a]pyrazolo[4,3-e]pyrimidin-4(2H)-one

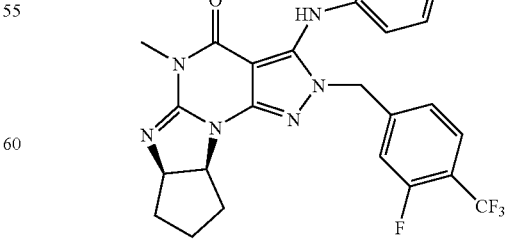

The synthesis method is analogous to example 2 wherein (1R,2R)-2-amino-cyclopentanol is added in step (d) instead of trans-2-amino-cyclohexanol hydrochloride; and 3-fluoro-4-trifluoromethyl-benzyl bromide is added in step (f) instead of benzoylbenzyl bromide.

Example 23

(6aR,9aS)-3-(phenylamino)-5,6a,7,8,9,9a-hexahydro-5-methyl-2-(4-methylsulfonyl-benzyl)-cyclopent[4,5]imidazo[1,2-a]pyrazolo[4,3-e]pyrimidin-4(2H)-one

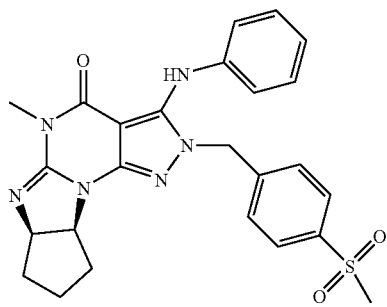

The synthesis method is analogous to example 2 wherein (1R,2R)-2-amino-cyclopentanol is added in step (d) instead of trans-2-amino-cyclohexanol hydrochloride; and p-methylsulfonyl-benzyl bromide is added in step (f) instead of benzoylbenzyl bromide.

Example 24

Measurement of PDE1B Inhibition in vitro Using IMAP Phosphodiesterase Assay Kit

Phosphodiesterase 1B (PDE1 B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay
Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerlkinElmer, Shelton, Conn.) to measure the fluorescence polarization (Δmp).

A decrease in GMP concentration, measured as decreased Δmp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus ΔmP, which allows $IC_{50}$ values to be estimated using nonlinear regression software (XLFit; IDBS, Cambridge, Mass.).

The compounds of Examples 1-14 have $IC_{50}$ values of less than 1 μM in this assay, generally less than 10 nM.

The invention claimed is:
1. A compound of Formula III:

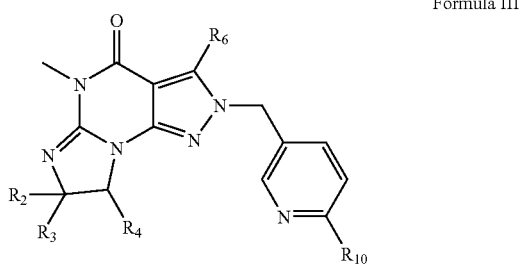

Formula III wherein
$R_2$ is H and $R_3$ and $R_4$ together form a tri- or tetra-methylene bridge;
$R_6$ is phenylamino or benzylamino;
$R_{10}$ is haloalkyl, phenyl, pyridyl, or thiadiazolyl;
wherein
phenyl is optionally substituted with $C_{1-4}$alkyl, halogen, halo$C_{1-4}$alkyl, hydroxy, $C_{1-4}$carboxy or an additional aryl or heteroaryl; or
pyridyl or thiadiazolyl is optionally substituted with $C_{1-4}$alkyl, halogen, halo$C_{1-4}$alkyl, hydroxy or $C_{1-4}$carboxy;
in free, salt or physiologically hydrolysable and acceptable ester prodrug form.

2. A compound of Formula IV

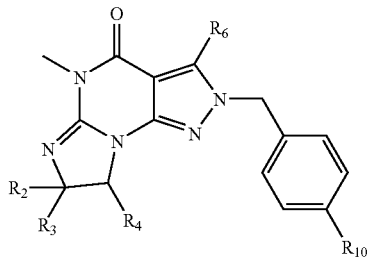

Formula IV wherein
R$_2$ is H and R$_3$ and R$_4$ together form a tri- or tetra-methylene bridge;
R$_6$ is phenylamino or benzylamino;
R$_{10}$ is phenyl, pyridyl, or thiadiazolyl,
wherein
phenyl is optionally substituted with C$_{1-4}$alkyl, halogen, haloC$_{1-4}$alkyl, hydroxy, C$_{1-4}$carboxy or an additional aryl or heteroaryl; or
pyridyl or thiadiazolyl is optionally substituted with C$_{1-4}$alkyl, halogen, haloC$_{1-4}$alkyl, hydroxy or C$_{1-4}$carboxy;
in free, salt or physiologically hydrolysable and acceptable ester prodrug form.

3. A compound selected from the following:
Cis-(6aR*,10aS*)-1-(4-Benzoylbenzyl)-5,6a,7,8,9,10,10a-heptahydro-5-methyl-3-(phenylamino)cyclohex[4,5]imidazo[1,2-a]pyrazolo[4,3-e]pyrimidin-4(1H)-one;
Cis-(6aR*,10aS*)-5,6a,7,8,9,10,10a-heptahydro-5-methyl-3-(phenylamino)-1-(4-(pyridin-2-yl)benzyl)benzyl)-cyclohex[4,5]imidazo[1,2-a]pyrazolo[4,3-e]pyrimidin-4-(1H)-one;
Cis-(6aR*,10aS*)-2-(4-(Pyridin-2-yl)benzyl)-5,6a,7,8,9,10,10a-heptahydro-5-methyl-3-(phenylamino)cyclohex[4,5]imidazo[1,2-a]pyrazolo[4,3-e]pyrimidin-4(2H)-one;
Cis-(6aR*,10aS*)-3-(Benzyl)-5,6a,7,8,9,10,10a-heptahydro-5-methyl-2-(4-(1,2,3-thiadiazol-4-yl)benzyl)-cyclohex[4,5]imidazo[1,2-a]pyrazolo[4,3-e]pyrimidin-4(2H)-one;
Cis-(6aR*,10aS*)-3-(Benzyl)-2-(4-Biphenyl-4-ylmethyl)-5,6a,7,8,9,10,10a-heptahydro-5-methyl-cyclohex[4,5]imidazo[1,2-a]pyrazolo[4,3-e]pyrimidin-4(2H)-one;
(6aR,9aS)-5,6a,7,8,9,9a-hexahydro-5-methyl-3-(phenylamino)-2-(4-Pyridin-2-yl)-benzyl)-cyclopent[4,5]imidazo[1,2-a]pyrazolo[4,3-e]pyrimidin-4(2H)-one;
(6aR,9aS)-5,6a,7,8,9,9a-hexahydro-5-methyl-3-(phenylamino)-1-(4-Pyridin-2-yl)-benzyl)-cyclopent[4,5]imidazo[1,2-a]pyrazolo[4,3-e]pyrimidin-4(1H)-one;
(6aR,9aS)-3-(benzylamino)-5,6a,7,8,9,9a-hexahydro-5-methyl-2-(4-Pyridin-2-yl)-benzyl)-cyclopent[4,5]imidazo[1,2-a]pyrazolo[4,3-e]pyrimidin-4(2H)-one;
(6aR,9aS)-3-(phenylamino)-5,6a,7,8,9,9a-hexahydro-5-methyl-2-(biphenyl-4-ylmethyl)-cyclopent[4,5]imidazo[1,2-a]pyrazolo[4,3-e]pyrimidin-4(2H)-one;
(6aR,9aS)-3-(phenylamino)-5,6a,7,8,9,9a-hexahydro-5-methyl-2-(4-(trifluoromethyl)-benzyl)-cyclopent[4,5]imidazo[1,2-a]pyrazolo[4,3-e]pyrimidin-4(2H)-one;
(6aR,9aS)-3-(phenylamino)-5,6a,7,8,9,9a-hexahydro-5-methyl-2-((6-trifluoromethyl)-pyridin-3-yl)methyl)-cyclopent[4,5]imidazo[1,2-a]pyrazolo[4,3-e]pyrimidin-4(2H)-one;
(6aR,9aS)-3-(phenylamino)-5,6a,7,8,9,9a-hexahydro-5-methyl-2-(3-fluoro-4-(trifluoromethyl)-benzyl)-cyclopent[4,5]imidazo[1,2-a]pyrazolo[4,3-e]pyrimidin-4(2H)-one; and
(6aR,9aS)-3-(phenylamino)-5,6a,7,8,9,9a-hexahydro-5-methyl-2-(4-methylsulfonyl-benzyl)-cyclopent[4,5]imidazo[1,2-a]pyrazolo[4,3-e]pyrimidin-4(2H)-one;
in free or salt form, or in pure enantiomeric form.

4. A method of treating any of the following conditions: Parkinson's disease, restless leg, tremors, dyskinesias, Huntington's disease, Alzheimer's disease, and drug-induced movement disorders; attention deficit disorder, attention deficit hyperactivity disorder, bipolar illness, cognitive impairment, dementia, and/or drug addiction; pulmonary hypertension; or chronic obstructive pulmonary disease, comprising administering an effective amount of a compound according to claim 2 in free, pharmaceutically acceptable salt, physiologically hydrolysable and acceptable ester prodrug or pure enantiomeric form to a patient in need of such treatment.

5. The method of claim 4 wherein the condition is Parkinson's disease.

6. The method of claim 4 wherein the condition is cognitive impairment.

7. A method of making a compound according to claim 2 comprising reacting a compound of Formula IIIJ:

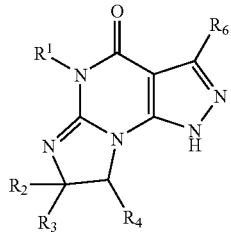

(IIIJ)

wherein R$_1$ is methyl, R$_{2-4}$ and R$_6$ are as defined in claim 2 for Formula IV, with a compound of formula X—CH$_2$-(4-phenyl)-R$_{10}$ wherein X is a leaving group and R$_{10}$ is as defined in Formula IV according to claim 2, the compound according to claim 2 thus obtained.

8. A method of making a compound according to claim 2 comprising dehydrating the compound:

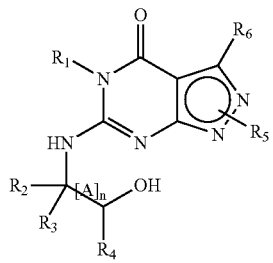

wherein R$_1$ is methyl, R$_5$ is —CH$_2$-(4-phenyl)-R$_{10}$, R$_{2-4}$ and R$_6$ are as defined in claim 2, and recovering the compound according to claim 2.

9. The compound according to claim 2, wherein R$_2$ is H and R$_3$ and R$_4$ together form a tri- or tetra-methylene bridge wherein the carbons carrying R$_3$ and R$_4$ have the R and S configuration respectively, in free, salt or physiologically hydrolysable and acceptable ester prodrug form.

10. The compound according to claim 2, wherein R₂ is H and R₃ and R₄ together form a tri-methylene bridge wherein the carbons carrying R₃ and R₄ have the R and S configuration respectively, in free, salt or physiologically hydrolysable and acceptable ester prodrug form.

11. The compound according to claim 2, wherein R₁₀ is phenyl optionally substituted with C₁₋₄alkyl, halogen, haloC₁₋₄alkyl, hydroxy, C₁₋₄carboxy or an additional aryl or heteroaryl, in free, salt or physiologically hydrolysable and acceptable ester prodrug form.

12. The compound according to claim 2, wherein R₁₀ is pyrid-2-yl or 1,2,3-thiadiazol-4-yl, optionally substituted with C₁₋₄alkyl, halogen, haloC₁₋₄alkyl, hydroxy, C₁₋₄carboxy or an additional aryl or heteroaryl, in free, salt or physiologically hydrolysable and acceptable ester prodrug form.

13. The compound according to claim 2, wherein R₆ is phenylamino optionally substituted with C₁₋₄alkyl, halogen, haloC₁₋₄alkyl, hydroxy, C₁₋₄carboxy or an additional aryl or heteroaryl, in free, salt or physiologically hydrolysable and acceptable ester prodrug form.

14. The compound according to claim 2, wherein said compound is (6aR,9aS)-5,6a,7,8,9,9a-hexahydro-5-methyl-3-(phenylamino)-(2-(4-pyridin-2-yl)-benzyl)-cyclopent[4,5]imidazo[1,2-a]pyrazolo[4,3-e]pyrimidin-4(2H)-one in free or salt or pure enantiomeric form.

15. A pharmaceutical composition comprising a compound of Formula III:

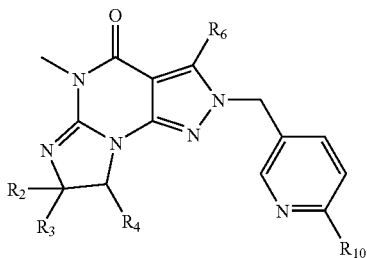

Formula III wherein
R₂ is H and R₃ and R₄ together form a tri- or tetra-methylene bridge;
R₆ is phenylamino or benzylamino;
R₁₀ is haloalkyl, phenyl, pyridyl, or thiadiazol,
wherein
phenyl is optionally substituted with C₁₋₄alkyl, halogen, haloC₁₋₄alkyl, hydroxy, C₁₋₄carboxy or an additional aryl or heteroaryl; or
pyridyl or thiadiazolyl is optionally substituted with C₁₋₄alkyl, halogen, haloC₁₋₄alkyl, hydroxy or C₁₋₄-carboxy;
in free or pharmaceutically acceptable salt or physiological hydrolysable and acceptable ester prodrug form, in admixture with a pharmaceutically acceptable diluent or carrier.

16. A pharmaceutical composition comprising a compound of Formula IV

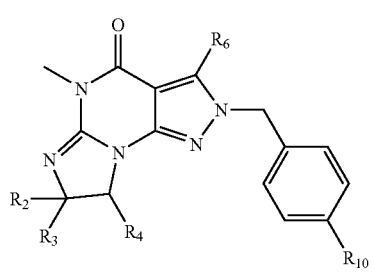

Formula IV wherein
R₂ is H and R₃ and R₄ together form a tri- or tetra-methylene bridge;
R₆ is phenylamino or benzylamino;
R₁₀ is phenyl, pyridyl, or thiadiazolyl;
wherein
phenyl is optionally substituted with C₁₋₄alkyl, halogen, haloC₁₋₄alkyl, hydroxy, C₁₋₄carboxy or an additional aryl or heteroaryl; or
pyridyl or thiadiazolyl is optionally substituted with C₁₋₄alkyl, halogen, haloC₁₋₄alkyl, hydroxy or C₁₋₄carboxy;
in free or pharmaceutically acceptable salt or physiological hydrolysable and acceptable ester prodrug form, in admixture with a pharmaceutically acceptable diluent or carrier.

17. A pharmaceutical composition comprising a compound selected from the group consisting of:
Cis-(6aR*,10aS*)-1-(4-Benzoylbenzyl)-5,6a,7,8,9,10,10a-heptahydro-5-methyl-3-(phenylamino)cyclohex[4,5]imidazo[1,2-a]pyrazolo[4,3-e]pyrimidin-4(1H-one;
Cis-(6aR*,10aS*)-5,6a,7,8,9,10,10a-heptahydro-5-methyl-3-(phenylamino)-1-(4-(pyridin-2yl)benzyl)benzyl)-cyclohex[4,5]imidazo[1,2-a]pyrazolo[4,3-e]pyrimidin-4-(1H)-one;
Cis-(6aR*,10aS*)-2-(4-(Pyridin-2-yl)benzyl)-5,6a,7,8,9,10,10a-heptahydro-5-methyl-3-(phenylamino)cyclohex[4,5]imidazo[1,2-a]pyrazolo[4,3-e]pyrimidin-4(2H)-one;
Cis-(6aR*,10aS*)-3-(Benzyl)-5,6a,7,8,9,10,10a-heptahydro-5-methyl-2-(4-(1,2,3-thiadiazol-4-yl)benzyl)-cyclohex[4,5]imidazo[1,2-a]pyrazolo[4,3-e]pyrimidin-4(2H)-one;
Cis-(6aR*,10aS*)-3-(Benzyl)-2-(4-Biphenyl-4-ylmethyl)-5,6a,7,8,9,10,10a-heptahydro-5-methyl-cyclohex[4,5]imidazo[1,2-a]pyrazolo[4,3-e]pyrimidin-4(2H)-one;
(6aR,9aS)-5,6a,7,8,9,9a-hexahydro-5-methyl-3-(phenylamino)-2-(4-Pyridin-2-yl)-benzyl)-cyclopent[4,5]imidazo[1,2-a]pyrazolo[4,3-e]pyrimidin-4(2H)-one;
(6aR,9aS)-5,6a,7,8,9,9a-hexahydro-5-methyl-3-(phenylamino)-1-(4-Pyridin-2-yl)-benzyl)-cyclopent[4,5]imidazo[1,2-a]pyrazolo[4,3-e]pyrimidin-4(1H)-one;
(6aR,9aS)-3-(benzylamino)-5,6a,7,8,9,9a-hexahydro-5-methyl-2-(4-Pyridin-2-yl)-benzyl)-cyclopent[4,5]imidazo[1,2-a]pyrazolo[4,3-e]pyrimidin-4(2H)-one;
(6aR,9aS)-3-(phenylamino)-5,6a,7,8,9,9a-hexahydro-5-methyl-2-(biphenyl-4-ylmethyl)-cyclopent[4,5]imidazo[1,2-a]pyrazolo[4,3-e]pyrimidin-4(2H)-one;

(6aR,9aS)-3-(phenylamino)-5,6a,7,8,9,9a-hexahydro-5-methyl-2-(4-(trifluoromethyl)-benzyl)-cyclopent[4,5]imidazo[1,2-a]pyrazolo[4,3-e]pyrimidin-4(2H)-one;

(6aR,9aS)-3-(phenylamino)-5,6a,7,8,9,9a-hexahydro-5-methyl-2-((6-trifluoromethyl)-pyridin-3-yl)methyl)-cyclopent[4,5]imidazo[1,2-a]pyrazolo[4,3-e]pyrimidin-4(2H)-one;

(6aR,9aS)-3-(phenylamino)-5,6a,7,8,9,9a-hexahydro-5-methyl-2-(3-fluoro-4-(trifluoromethyl)-benzyl)-cyclopent[4,5]imidazo[1,2-a]pyrazolo[4,3-e]pyrimidin-4(2H)-one; and (6aR,9aS)-3-(phenylamino)-5,6a,7,8,9,9a-hexahydro-5-methyl-2-(4-methylsulfonyl-benzyl)-cyclopent[4,5]imidazo[1,2-a]pyrazolo[4,3-e]pyrimidin-4(2H)-one;

in free or pharmaceutically acceptable salt form, or in pure enantiomeric form, in admixture with a pharmaceutically acceptable diluent or carrier.

18. The pharmaceutical composition according to claim 17, wherein said compound is (6aR,9aS)-5,6a,7,8,9,9a-hexahydro-5-methyl-3-(phenylamino)-2-(4-Pyridin-2-yl)-benzyl)-cyclopent[4,5]imidazo[1,2-a]pyrazolo[4,3-e]pyrimidin-4(2H)-one in free or pharmaceutically acceptable salt or in pure enantiomeric form.

19. The method according to claim 8, wherein said method comprises the use of thionyl chloride.

20. The compound according to claim 2, wherein $R_{10}$ is pyridyl substituted with $C_{1-4}$alkyl, halogen, halo$C_{1-4}$alkyl, hydroxy or $C_{1-4}$carboxy, in free, pharmaceutically acceptable salt or physiological hydrolysable and acceptable ester prodrug form.

21. The compound according to claim 20, wherein $R_6$ is phenylamino, in free, pharmaceutically acceptable salt or physiological hydrolysable and acceptable ester prodrug form.

* * * * *